US009491277B2

(12) United States Patent
Vincent

(10) Patent No.: US 9,491,277 B2
(45) Date of Patent: Nov. 8, 2016

(54) COMPUTERIZED METHOD AND SYSTEM FOR GLOBAL HEALTH, PERSONAL SAFETY AND EMERGENCY RESPONSE

(71) Applicant: Melissa Vincent, Beverly Hills, CA (US)

(72) Inventor: Melissa Vincent, Beverly Hills, CA (US)

(*) Notice: Subject to any disclaimer, the term of this patent is extended or adjusted under 35 U.S.C. 154(b) by 0 days.

(21) Appl. No.: 14/677,973

(22) Filed: Apr. 3, 2015

(65) Prior Publication Data

US 2015/0288797 A1    Oct. 8, 2015

Related U.S. Application Data

(60) Provisional application No. 62/077,882, filed on Nov. 10, 2014, provisional application No. 62/039,422, filed on Aug. 20, 2014, provisional application No. 62/038,974, filed on Aug. 19, 2014, provisional application No. 61/974,440, filed on Apr. 3, 2014.

(51) Int. Cl.

| H04M 1/725 | (2006.01) |
|---|---|
| H04W 4/02 | (2009.01) |
| H04W 4/22 | (2009.01) |
| G06F 19/00 | (2011.01) |
| G06Q 50/18 | (2012.01) |
| G06Q 10/10 | (2012.01) |

(52) U.S. Cl.
CPC ........ *H04M 1/72538* (2013.01); *G06F 19/322* (2013.01); *G06F 19/3418* (2013.01); *G06Q 10/10* (2013.01); *G06Q 50/186* (2013.01); *H04W 4/02* (2013.01); *H04W 4/22* (2013.01)

(58) Field of Classification Search
CPC ......... H04W 4/02; H04W 4/22; H04W 4/16; H04W 4/20; H04M 1/72538; G06F 9/322; G06F 19/3418; G06Q 10/10; G06Q 50/186; A61J 7/0481
See application file for complete search history.

(56) References Cited

U.S. PATENT DOCUMENTS

| 6,985,771 | B2 | 1/2006 | Fischell et al. |
|---|---|---|---|
| 7,520,419 | B2 | 4/2009 | Libin et al. |
| 8,483,812 | B2 | 7/2013 | Fischell et al. |
| 8,684,922 | B2 | 4/2014 | Tran |
| 8,949,738 | B2 * | 2/2015 | Felt ................. G06F 19/326 705/2 |
| 8,970,381 | B2 * | 3/2015 | Heath ............... G06F 19/322 340/573.1 |
| 2003/0230590 | A1 * | 12/2003 | Gilmore ..................... 221/2 |
| 2006/0215495 | A1 * | 9/2006 | Soled et al. ............... 368/10 |

(Continued)

FOREIGN PATENT DOCUMENTS

JP         2001190504        7/2001

*Primary Examiner* — Hirdepal Singh
(74) *Attorney, Agent, or Firm* — Carrie Stroup

(57) ABSTRACT

A computerized system and method for intuitively detecting a user's need for emergency help, preventive care and medical interventions and also for coordinating care for user's loved ones and pets when user experiences an emergency or has passed away. Detection is done via labs and life signs equipment and sensors, self-initiated request for monitoring or the system's periodically polling user through an alert, a telephone call, a notification, a text message or other appropriate means to find out if they are in danger. Polling and automated monitoring may also be triggered by real-time medical data electronically or wirelessly transmitted to the system. If user fails to respond, the system automatedly calls either user's contacts (by listed priority) to notify them of a potential emergency, or emergency responders directly depending on severity of the emergency and communicates to them critical information as well as a code to access user's medical record(s).

18 Claims, 44 Drawing Sheets

(56) References Cited

U.S. PATENT DOCUMENTS

| | | | |
|---|---|---|---|
| 2008/0013705 A1* | 1/2008 | Yoffie et al. | 379/201.12 |
| 2009/0088607 A1* | 4/2009 | Muraca | 600/300 |
| 2009/0198696 A1 | 8/2009 | Banks | |
| 2011/0125866 A1 | 5/2011 | Williams | |
| 2012/0252401 A1* | 10/2012 | Rothschild | G08B 25/001 455/404.2 |
| 2012/0278865 A1 | 11/2012 | Sawdy | |
| 2013/0095459 A1* | 4/2013 | Tran | 434/247 |
| 2013/0179472 A1 | 7/2013 | Junqua et al. | |
| 2015/0002293 A1* | 1/2015 | Nepo | G08B 15/004 340/539.13 |
| 2016/0014584 A1* | 1/2016 | Webb | H04W 4/22 455/404.2 |
| 2016/0165425 A1* | 6/2016 | Diamond | H04W 12/06 455/404.2 |

* cited by examiner

COMPUTERIZED METHOD AND SYSTEM FOR GLOBAL HEALTH, PERSONAL SAFETY AND EMERGENCY RESPONSE

PRIORITY CLAIM

This application claims the benefit of U.S. Provisional Patent Application No. 62/077,882, filed Nov. 10, 2014, and entitled "Computerized Method and System for Global Health, Personal Safety and Emergency Response".

This application claims the benefit of U.S. Provisional Patent Application No. 62/039,422, filed Aug. 20, 2014, and entitled "Computerized Method and System for Global Health, Personal Safety and Emergency Response".

This application also claims the benefit of U.S. Provisional Patent Application No. 62/038,974, filed Aug. 19, 2014, and entitled "Computerized Method and System for Global Health, Personal Safety and Emergency Response".

This application claims the benefit of U.S. Provisional Patent Application No. 61/974,440, filed Apr. 3, 2014, and entitled "Method and System for Global Health and Emergency Response".

All of the above patent applications are hereby incorporated herein by reference in their entireties.

COPYRIGHT NOTICE

A portion of the disclosure of this patent document contains material that is subject to copyright protection. The copyright owner has no objection to the facsimile reproduction by anyone of the patent document or patent disclosure as it appears in the Patent and Trademark Office, patent file or records, but otherwise reserves all copyright rights whatsoever.

FIELD OF THE DISCLOSURE

The present disclosure is generally related to a network based service and/or a mobile app for: (i) automatedly alerting emergency responders when a user is incapacitated and unable to do so for themselves, (ii) allowing health entities to easily access, communicate, and share up-to-date electronic health records of patients, (iii) preventing certain illnesses, (iv) diagnosing alerting to changes in medical conditions as well as suggesting treatment to discuss with a doctor, (vi) protecting dependents left behind, and (vii) helping beneficiaries locate inherited assets.

BACKGROUND OF THE DISCLOSURE

Previously, individuals living alone who could not physically access their phone to call for help at the time of an emergency or who could not physically push a "911 button" on a 911 app on their cell phone, or an emergency button on their Life-Alert devices or other similar systems—either because they forgot they were wearing Life-Alert devices, or were too weak or too sick to push the button or simply unable to push a button having passed out before they could push it—were left unattended and non-rescued for hours at a time. In some cases this resulted in death, severe injuries, and paralysis that could easily have been prevented had they been rescued on time. The disclosed system fills that void. This is a new, unique and nonobvious global health, personal safety, and emergency response system designed to provide protection for individuals at risk of critical illnesses or fatal accidents, by alerting help at the moment it is needed and providing critical information to emergency professionals.

In contrast to existing alert systems, this invention does not require the individual to press any button or take similar action to call for help—a physical action that may be impossible in a critical situation. The fact is accidents and illnesses happen to everyone. With this system, users no longer have to be powerless witnesses to their own sad fate. They can download this system to their computing device (e.g. smartphone) and the system will recognize when they are in danger and get them timely emergency help anywhere in the world, even if they are unconscious and even if their phone is not at a close distance. Users no longer have to be alone again even when they are by themselves. They can have this system serve as their loyal companion. The system comprises a mobile device app, a web application, white label APIs, advanced communications center services, a research center, a health resource sharing platform and a global health network. The system can also be used with other hardware and regular telephone services. The system includes its own technology, its own telephony and GPS systems, existing technology, future technology, its own or existing Content Distribution Networks (CDNs) or load balancing for data routing management and various hardware and accessories that serve to complement its efficacy.

Likewise, individuals who did not have a preset social and legal arrangements and/or a will and trusts in place ran the risks of having their assets unclaimed by their dependents, next of kin, loved ones and therefore ran the risks of causing their dependents to suffer the consequences of the lack thereof of these documents. This computer system fills that void.

Also, individuals whose health information was unknown by a doctor or a medical treatment team oftentimes receive an erroneous diagnosis, inaccurate treatments and/or duplicate treatments, duplicate diagnostic studies such as CT-Scan, X-ray etc., duplicate medications prescriptions, etc. Previously, individuals at risk for a condition or disease might not be aware of their risk(s) until it was too late when they consult a doctor or die from it. As a result, a once preventable disease becomes a real disease or a death sentence. Likewise previously, hospitals, other health entities and individuals who wanted to transmit medical records to another hospital, doctor, or other health entities could only do so using either mail, email or fax putting patients' medical records at risk of falling into the wrong hands. The various embodiments of the present disclosure fill that void by putting the security control, privacy and confidentiality of a user's electronic medical health records into the user's hands. The user can setup the system so that it does what the user wants it to do. Every user has the right to require that their health information be kept confidential. With this system, not only transmissions can be blocked, but also all transmissions are encrypted, tracked and leave an audit trail. This system allows users to transmit their medical records securely and seamlessly, whether it be in electronic form, paper form, photo, video or other forms, using the computer system and secure internet connection to transfer, synchronize, auto-update, scan in, embed and remotely access information via a user interface, a web server, APIs (Application Programming Interface: software to software interface), web APIs, and/or by other means adequate and compatible. The system allows users to create high security lockout access and allows users to place record holds, use role-based access (determining/authorizing in advance what individual or group of individuals can access a particular record/information) and use aliases for anonymity or to mask their identity along with de-identification mechanism.

They may also choose to identify themselves using a set of numbers or a combination of numbers and letters than by their names; and, to request that this set of numbers or combination of numbers and letters be used in lieu of their names. The system is able to connect the alias or alternative identification by numbers or a combination of numbers and letters back to the user's (e.g. patient's) legal name and account number in a secure manner and via secure channels. Users control who sees and/or accesses their health records and for how long. Users control what those with access can do with their information. Users can put their record on hold or lock down their entire medical records or part of it. With this computer system, the user can give screening access only, restrict printing and downloading, make their record disappear when the clock reaches a specified period of time set, require rigid login using a set of access code(s), password, signatures, pin, or fingerprint, iris or facial recognition. Users can revoke or block access to just a specific section of their chart, for example, a lab result, a treatment or a progress note containing HIV-related information. Users can track all changes including addendums and all versions of their medical records and or mask sensitive entries etc. In the same fashion, the computer system may also restrict access to the network if it detects a remote connection that is not secure, so that the user's information can remain secure.

Current typical emergency response system requires pendants or wristbands to be worn by individuals, and alerts for help when the user presses a button. Similar functionality is available in various mobile device emergency apps currently on the market. However, none of them are equipped with systems to recognize when users are incapacitated or otherwise unable to summon help. This computer system allows a user to receive automated emergency help even if the user is unconscious (with no need to press a button, dial a number or take any action whatsoever when they need emergency help). This system does not require any contact of any kind with the user. No action is needed; except that the app is turned on to begin with. For example, if a user experiences a heart attack, stroke, seizures, drug overdose, syncope, critical vital signs, pacemaker malfunction, diabetic crisis or other emergencies, the app alerts 911 and communicates their exact conditions and circumstances to medical personnel. That means EMTs and law enforcement can know what has happened before they arrive on the scene. Since the system has location information (preprogrammed and/or GPS) and has the option for preprogramming a host of medical and other information, it ensures that emergency responders will show up at the right address and have access to critical information. The information included can include details about illnesses and medications as well as about who to contact if the individual is unable to communicate. Users have total control over their privacy and confidentiality. Doctors can easily gain permitted access to the user's current medical records, to avoid over-medicating and mis-diagnosing them without needing to access the user's phone. User's wishes are relayed. If a user becomes ill or injured and their children are under 18, the system will relay the name and address of user's preferred caregiver for the children, even if users are too ill or injured to communicate without needing to access the user's phone. Likewise, if the user passes away, the system makes sure their wishes regarding their children's care and their projects are respected. Pre-death, the user can pre-program management for their minor's lives up to the point they legally become adults. If the user was working on a project, the project can continue its pathway through the system Research Center and the resulting revenues are distributed among user's indicated beneficiaries. This ensures the safety, peace-of-mind and well-being of users and their loved ones both while the user is alive and after the user's demise. These features are referred to as a user Digital Clone and Post-Life Dependent & Project Management. This feature is quasi-comparable to having the user alive and managing their children's lives. It can save comprehensive data about the users and their dependents, all aspects of their lives, their finances, their wishes, wants and desires for themselves and their dependents and users can pre-subscribe for any numbers of years desired. Users' medical and legal documents are kept safely on file and up-to-date. The computer system can be used anywhere in the world and all a user needs to benefit from the system is a smartphone, or a portable or non-portable computer. If users wish, they can leave the app on all the time for continuous or random monitoring and user also has the choice of aborting any of the modes (monitoring, pre-emergency and emergency) at any time and any point in time; but will be asked to confirm/verify that order/decision. The system incorporates multi-language voice-to-voice, voice-to-text, text-to-text, text-to-voice translation and voice recognition features so that users can speak in their desired language as well as type in the word or phrase they want translated and then transmits in real time and receives in real time either an audio response or a text or both a text and audio response which is crucial in conversations between doctors who speak different languages and in conversation with patients who speak different languages. The system will be able to communicate with users and health professionals in their native or selected languages using a combination of voice recognition, speech-to-speech and text-to-speech technology. For example, Mila speaks only Spanish but travels to Russia, gets sick there, and has to see a Russian doctor who speaks only Russian. Mila either sets up her preferred language and the translation desired or lets the system determine the languages in question as she establishes connection/contact with the Russian doctor. Upon establishing connection, the system determines the different languages spoken by the two by analyzing the inputted words/info or by analyzing Mila's inputted preferred/selected language against the Russian doctor preferred/selected language and vice versa. Translation is automatedly initiated accordingly to enable the Russian doctor to hear/read Mila's conversation in the Russian language in real time and to enable Mila to hear/read the Russian doctor in the Spanish language as if they were both speaking the same language. The system uses geographic tracking to identify appropriate emergency numbers and the local language in which the emergency alert and message is to be delivered along with their preferred method of message delivery. The computer system also has provisions for cases of abduction and kidnapping where the offender gets rid of the victim's phone. To allow a user to still be trackable and receive emergency help, the computer system pairs the application with a wearable hidden miniature Global Position System (GPS) tracking device a user can wear for that extra shield of safety to still be track-able. This system is the first of its kind requiring no input from the user in case of emergency, even if the user is unconscious. Users will not have to be near computers and base stations, nor will they have to wear pendants or bracelets. Users will not even have to press a button, an action which may be impossible in an emergency. The system's primary mission is to reduce preventable deaths and disabilities by offering a life-saving product available to everyone in the world and empower people through technology to be in control of their own health and private information, no matter who they are, or where they live. Think of this system as a loyal companion, a faithful angel, or a really intelligent caregiver who is there for the user whenever he/she needs it.

Systems like Life-Alert and its competitors, and the 911 apps and others currently on the market, allow users only to "physically" push a button, either on their phone or on an accessory. Therefore, these systems do not address cases in which users cannot physically push a button or lack access to their phone at the very time they have the emergencies. Examples include situations such as when a user experiences a sudden loss of consciousness/syncopal episode or a mechanical fall in the shower, has poor memory and forgets they were wearing a Life-Alert bracelet, or falls at a distance from the phone and is unable to get up. Also, sometimes the user is so sick and/or so weak that they cannot talk or explain what is happening. In other words, previous systems are inefficient and also very $19^{th}$ century. With the present disclosure, wearing bracelets or any other accessories that require the push of a button to provide emergency rescue help or needing a phone close by to call for emergency help will be a thing of the past.

Likewise, systems such as Life-Alert or similar, such as Connect America and LifeWatch USA, and the 911 apps on the market all are limited to touch/push/press/click of a button. However, what happens when a user cannot push that button or is too far from their phone? For example, an elderly patient wearing a Life-Alert necklace fell on her bathroom floor after taking a shower and she was unable to get up. Her Life-Alert necklace would have been useful had she remembered to use it. Unfortunately, being elderly with poor memory, she did not remember she was wearing a Life-Alert necklace. She remained lying down on the cold bathroom floor for eight and a half hours before she was rescued. She was found dehydrated, hypothermic, in pain from a broken hip with accompanying internal bleeding, starving and shaking in fear that she was going to die on the bathroom floor. Consider a sitting person who had a severe headache for an hour and subsequently develops a massive stroke and therefore is unable to press the button on their necklace or a young person who decides to experiment with drugs in the privacy of his/her room but is not sure what to expect and has no idea this would end up causing his/her death. The present disclosure helps save those lives that would otherwise end early/prematurely.

Another problem not addressed by the prior art is distance with transmitting from the wearer to a base unit nearby. What happens when the user leaves their house or travels? To mitigate this problem, some companies provide the user with a separate cell phone to call if for emergency help. This combination forces a user to carry two cell phones: one for personal use and one for emergency response. The present disclosure solves this problem by providing boundless worldwide coverage with the same simplistic system. For example, if a user lives in Europe or travels to Europe, he/she won't need to make any changes to receive automated emergency help because the computer system is intelligent enough to automatically self-adjust and deliver messages in the location's native language.

One other problem not addressed by these apparatuses with mobile apps and life alert systems currently on the market is loss of power and no phone signal. With these systems, if the battery dies, then so does the help their system offers. The present disclosure solves this issue by providing a "charge-device" reminder and/or by alerting a user to charge their phone when it reaches a preset parameter and/or by remotely detecting inactive interfaces of up-to-date subscriptions of the innovative app installed on a user's apparatus (e.g. electronic computing device smartphone with mobile app), which incorporates a series of codes/algorithms, which, when an app becomes inactive (not by the user's choice) such as when the apparatus is out of power or malfunctioning, automatically activate the "No Signal or protocol" comprising: 1) forced reboot/refresh of the system; 2) a call/text/alert to a pre-selected neighbor or a relative who has close access to the user to go check on the user and/or 3) by offering the app's own dedicated/stand-alone apparatus/device with removable battery and/or with ultra-extended battery life that is able to last a longer usage than normal. As an added safety feature, if a user loses their phone while the app was on, access to the user's information can be remotely locked. Likewise, to allow users to use the computer system internationally and to counter the issue of running out of power on their regular phones, the system includes its own dedicated telephony and battery system and other accessories that complement the system.

No Phone Signal Safety. The system also has provisions for when the user's phone enters a No-Signal Zone. How is this done? As a user reaches or has reached a no-signal zone, the system detects "No Signal" and warns the user that he/she is entering a "No-signal zone". Warnings can be made in a manner preset by the user such as, for example, a special ringtone, beeping incessantly until user becomes aware and complies, etc. "Complying" as used herein means that if the signal is not restituted, the user already has a plan in place within the computer system to notify emergency contacts or loved ones of the user's intended location, if the user has not returned to a signal-zone after a certain period of time has elapsed.

On default settings, once the user approaches a no-signal zone, the computer system will automatically send an initial notice of last known location to the user's designated emergency contact(s) and will prompt users to input details of their trip/destination, how long the trip will last, or how long they plan to remain within the no-signal zone and when they expect to get back. The system can pick up on the user's arrival at home or at an indicated destination using location sensors. The system automatedly sends, or asks the user to approve, a second notice being sent to the same emergency contacts or loved one that were notified earlier to inform them this time around the user has arrived home or at a destination safe.

If a user did not attend to the phone on time and did not regain a signal, then the computer system will indicate how long since the last signal, and the precise location where the user last had a phone signal along with a map of their location. The user may then retrace their path to their latest signal zone, and they may call or send loved ones a message regarding their whereabouts. They may also put the computer system in monitoring mode.

International Travel Safety. For users who travel overseas and whose smartphone does not work overseas but take SIM cards (FIG. 38, 380), they can, if desired, obtain the computer system's proprietary international SIM cards compatible with the country they are visiting. Users can also purchase or borrow the system's own apparatus-smartphone as it will be inexpensive, unlocked, waterproof, and work globally since it supports three or more of the following global communication technologies: LTE, GSM, 4G, WCDMA/UMTS, HSPA, GPRS, EDGE, HSDPA, HSUPA, HSPA+, TD-LTE, FD-LTE, CDMA, EVDO etc.

SUMMARY OF THE DISCLOSURE

The various embodiments of the present disclosure describe a networked based computerized system and method for monitoring a user's health and safety status. The system can be used for "self-monitoring" by a user, elderly person, disabled person, etc., who is concerned that they may not be able to call emergency responders before they become incapacitated. The system may also be used for "remote-monitoring" by a third party affiliated with the patient, elderly person, etc. and who is concerned about their health and safety. Unless otherwise stated herein, the term "user" refers to a person who is "self-monitoring" or a person being monitored remotely.

In one embodiment, the system comprises a subscription service with a user's file stored in the user's apparatus comprising an electronic computing device (e.g. smartphone) and/or in the database of a remote server that communicates with a user's electronic computing device (e.g. smartphone) via a mobile app (i.e. computer program product) installed thereon. In another embodiment, the system further comprises a call center with live attendants who may remotely monitor a user at the user's request and call emergency responders (e.g. by contacting "911" resources) on behalf of the user, if required, in cases where the user prefers to deal with a live person versus their phone for whatever reason. Live attendants may also call emergency responders when an alarm is triggered, or when an alarm is triggered but does not call or deliver the emergency message effectively for whatever reason. Live attendants may also get involved to contact relatives or neighbors when an app goes out of power, or stops working in the middle of monitoring, or when the user's device is not working properly, or is unreliable etc.

The various embodiments of the present disclosure further comprise a computer program product installed on the user's apparatus (e.g. smartphone, desktop or laptop computer) to setup call back monitoring (i.e. "Monitoring Mode"), requiring that the a remote computer system call them at their designated time periods/intervals. If the user does not respond by answering the call, the computer system alerts their emergency contacts or indicated contacts (i.e. "Pre-Emergency Mode") to have the contact talk to the user, or call the user back within the requested time, or go physically check on the user. If the user has no contacts, or if the user or computer system determines that the user's medical condition is too serious to wait for contacts to intervene, then the computer system will call the emergency responders hotline (e.g. 911) (i.e. automatically switches to "Emergency Mode").

User setup. The user may register a user account using the computer program product (e.g. mobile app or web app's web-based subscription service), automated attendants, live attendants' service in person or online, their mobile service provider or any other means proven adequate. The person registering may be the direct user, and/or someone who wants to remotely monitor the user (e.g. an adult child of an elderly parent). The user or user's helper sets up the user's account on the system database either by selecting and filling out the section(s) applicable, by following a prompt and/or answering a few questions regarding themselves and their locations and residence(s), their health, current treatments, advance directives, special health concerns/requests, their emergency contacts, whether they have pets and/or dependents who need care if they are taken to a hospital, etc. The user is able to input their information manually, vocally, or by using any other means adequate and compatible.

The computer system is also able to store the user's health information in the memory of their apparatus (e.g. smartphone, laptop) and simultaneously store sensitive medical information and medical records in their account on the remote system database, such as a cloud based database. The user may access the database via the Medical interface that is accessible by the user at all times, but that is accessible by anyone other than the user, such as a private doctor or a health entity, only via the use of a code and a rigid and ultra-secure login. This is to ensure safety and security of the information and records. In the event of an emergency, the system informs the emergency responders (via the dispatcher on the 911 call) that there is a code to access the user's medical records, and once the user arrives at the hospital emergency room, the staff may use the code to contact the computer system via a computer network, e.g. the Internet, and access the medical records.

The user is also able to store legal documents on their account on the system database, such as a living will, last will and testament, etc. The documents can be accessed by an individual or an entity that has been given an access/authorization code, or that can provide a verifiable court order to the system. The system utilizes various sensors to monitor the user's status, comprising both their medical condition and their location. For example, the computer program product may automatically locate the user's current location with the user's permission or the user can input his/her exact address. The system may also receive real-time data on the user's medical condition via medical monitoring devices, such as the user's vital signs (heart rate, respiration, blood pressure, temperature, oxygen saturation), EKG, blood glucose, other blood work and tests such as blood sugar, EKGs etc. and other labs such as drug level, anemia, urinalysis, bacteria in urine, bacteria in the blood, strep throat, ear infections, and other.

Audio & Video/Sensors Detection Modes. The computer program product can be put on audio and/or video and/or sensor mode in any of the mode categories. In Audio Mode, the program uses audio features. In Video Mode, the program uses video features with or without audio, and the system's sensors are able to decipher if a user is not-moving/unresponsive/not breathing/has no pulse etc. for the app's automatic self-initiation of the Emergency mode. Video reports/images are included in the data recuperated using the confidential code (code can be obtained with the user's given or pre-given permission). In Video & Audio Mode, the program uses both features. For example, the computer program product's (i.e., app's) video system is embedded with fall detection sensors and an algorithm that, when a fall is detected, sets off the automated monitoring mode and/or pre-emergency mode and/or emergency mode on the app (which in turn can be turned off by users if faulty) and sends an alert to the 24/7 live communication support center so that the user can talk to a live monitoring agent.

Automated mode. The emergency number the app may call depends on the user's location. The app automatically locates the user's current location with the user's permission or the user can input his/her exact address. For the user's address, the user has the choice of inputting their zip code with the rest of the information populated by the program, or inputting their region, state, country, etc.

Users can set up their profile via phone with the support center, via the app website/web browser. directly from the app, or in person via onsite or at-home visit with an agent. The purpose of the user profile is to provide users with unlimited options when it comes to emergency rescue. Users can choose to have one emergency called/messaged/alerted, or multiple emergency contacts called/messaged/alerted one after one or simultaneously, or even have an entire group or community alerted. User can send instant real-time videos, audio, location and movement tracking to their emergency contacts, or to others they choose to share this information with. Individuals who are allowed access can see what is happening in the user's environment in real-time. Embedded GPS locators can give step-by-step walking and driving directions and distance to user's location. Parents can locate their children inside a supermarket by following the steps underlined for them. The advanced tracking system can be a lifesaver in case of abductions and domestic violence because law enforcement can be directed to the user's exact location. Likewise, an embedded "geo-fence" will allow users to set up alerts to be notified via push notifications, SMS or other applicable means whenever loved ones, such as special needs children or an elderly with Alzheimer's with a habit of wandering off, elopes, leaves or crosses a preset boundary. For privacy reasons, permissions from the monitored individual's phone will need to be obtained first. And for "anytime support" to users, a 24/7 live call and live chat system will be embedded directly into the system so that users need only to turn live support on to obtain live help. Likewise the app's video system is embedded with fall detection sensors and computation of motion-discriminating algorithms that, when a fall is detected, set off the automated monitoring mode and/or pre-emergency mode and/or emergency mode on app (which in turn can be turned off by users if faulty) and sends an alert to our 24/7 live communication support center so that the user can talk to a live monitoring agent.

When the user feels that they are in a situation requiring system monitoring, they input new commands or select from preset commands (how long they want to be checked on before the system is to proceed to calling emergency responders, etc. as well as select which preset situations applies to them. For example, a user could select the preset message, "I am feeling a bit dizzy" (to let emergency responders know what preceded their emergency situation) into their electronic computing device to have the system check on them by calling them on their phone (landline, smartphone, cell phone, PDA, etc.). For example, the user may be about to take a shower and is concerned about slipping and falling. They may use their smartphone or tablet or desktop computer to setup call back monitoring (i.e. "Monitoring Mode"), requiring that the system calls them at their designated time periods, and if they do not respond by answering the calls, then the system will alert their contacts (i.e. "Pre-Emergency Mode") to have them call or physical check on the user. If the user has no contacts, or the user or system determine that the user's medical condition is too serious to wait for contacts to intervene, then the system will call the emergency responders hotline (e.g. 911) (i.e. "Emergency Mode").

Monitoring Mode

After the program is put on "Monitoring mode," it will call/text/alert the user (using specific ringtones/sounds) at the preset intervals chosen by the user or at recommended scientifically proven intervals suggested by the app depending on the user's condition(s), signs and symptoms. The app keeps calling/texting/alerting the user in the same manner an alarm clock works until the user tells it to stop monitoring. If at any time, the user does not answer a call/text/alert (wherein user also decides how many rings), the app keeps ringing for the number of times, seconds or minutes pre-set. If the user does not answer by the end of the last ring, the computer system automatically switches to "Pre-Emergency mode" or "Emergency mode" depending on what the user has requested and possibly even bypasses the user's preset order in cases of critical conditions requiring immediate rescue (according to user's preset permission). This is also in the same manner that a real person would keep checking on the user and asking if they are OK, if the user had told the real person that they are not feeling quite well.

Pre-Emergency Mode

In the Pre-emergency mode, the app starts calling/messaging/alerting the user's emergency contacts or a pre-designated person by order of priority (as preset by the user: one by one or simultaneously) and for a predetermined number of seconds or minutes (as preset by the user). This is in the same way that a caregiver would alert a patient's emergency contacts if the patient stated that he/she was not feeling well.

If the user's first emergency contact does not answer, the computer system calls/texts/alerts the user's second emergency contact (if that's what the user had asked it to do) and so on in the exact order the user gave until it reaches one of the user's emergencies or until the user preset interval period to call 911 has been reached, in which case, it will automatically call 911 for the user. All these tasks are performed without the user having to lift a finger or having to be near their computer or mobile electronic computing device.

Note that the app can bypass the Pre-emergency mode also preset by the user and therefore go from "Monitoring mode" to "Emergency mode" if required and if user had given permission to the computer system to bypass his/her orders, as specified above. This is equivalent to an indirectly delayed (911 for USA) emergency call. The app can also save its automated communication exchange with the user's emergency contacts if this option was selected.

Emergency Mode

If the user did not answer a call/text/alert and/or their emergency contacts did not answer, the app automatically switches to "Emergency mode" and proceeds to call 911 (or the user's current location's emergency number in the city or country where they are to obtain immediate help). The user can also choose to put the program directly on "Emergency Mode" for the app to call 911 or the appropriate emergency number in a preset/set interval (second/minute/time). For example if the user selects Emergency Mode and 5 minutes and they are in the USA, the app will call 911 in 5 minutes. This gives the user time to cancel this order or prolong it if they decide that they are fine and no longer need immediate rescuing. This is the equivalent of asking a user's caregiver to call (911 for USA) if the user becomes non-responsive. Features include just the Emergency mode with indication of the number of minutes to elapse before the action of calling if the user does not stop the call. Each country is linked to its own medical emergency number.

The app goes two steps further:
1) It tells the emergency responder exactly what the user wants them to know, including health insurance, allergies, entire and updated medical info, emergency contact, next of kin etc. In contrast, a human caregiver may forget the user's exact directives and/or may not speak their language and/or may not be able to accurately communicate their health status to the paramedics or other medical professionals in an emergency situation.
2) The app allows space for the user's entire health record if the user approves. When the app calls for emergency responders, it gives the rescuer a code that the rescuer can use to obtain the user's confidential medical information from their personal computers if the user gave this permission and/or from their system. That code is given to those individuals or entities the user chose to give it to and also to licensed entities with a need-to-know that are involved in the user's treatment.

3) The app gives the user the ability to pass along a message regarding minor children, pets, stove, shower, windows, keys, and any other messages or instructions the user deems essential.
4) The doctor, nurse, and/or other hospital staff can access and add documents to user's medical folder on the system database using an access code.
5) Prescription safety. The system's advanced communication system allows doctors to seamlessly and securely issue orders and prescriptions through the computer system with an audit trail and users can route their prescriptions directly to the pharmacy of their choice. Medical folder can for example change color if a new order or prescription is in.

The system will also allow doctors as wells as patients and other health professionals to conduct audio and/or video conversations/conferences among themselves and with patients, patients' families, and/or other health professionals. Conference calls can be linked among health professionals, patients, and family members. Current treating doctor can for example communicate with other health professionals previously or presently involved in the care of a patient for further clarification about a given treatment. For example, a treating physician goes to a user's chart and sees that a Doctor Shadi previously saw the patient while the patient was traveling abroad. Because the system links every health professional to their contact information and also because the system allows connection to a global network as well as a chat room and conference call, the current treating physician can just click on Dr. Shadi's name to establish connection with Dr. Shadi directly from his screen. Dr. Shadi can choose to establish connection or not establish connection in a similar fashion as Skype or Gmail chat. The system will also incorporate a resource-sharing video hub in the form of YouTube® but the difference will be that this hub is reserved only for medical videos and users, and medical professionals can record their videos and upload in one from a single system (this system) as well put their videos on hold if they wish to hold broadcasting of it. Health professionals will be able to post videos and the public can post videos regarding health conditions.

6) Likewise the user's lawyer and lawyer's office can access and add documents to the user's legal folder using the code and the user can decide if they want to give them read access, add access or both.
7) The user is in control, the app does exactly what the user orders it to do, but the user can also choose to put the program on auto pilot.
8) The user can upload documents to their account in the system database, such as medical charts, power of attorney, advance directives, etc., upload insurance card and info, government ID, allergies, next of kin, DME at home, baseline vital signs, recent vital signs, recent blood sugar level, recent labs, recent EKGs, list of current medications, blood type, refuse blood, accept blood, advance directives, power of attorney, will, trusts documents, etc.

Various embodiments of the presently disclosed subject matter may include or be embodied in the form of computer-implemented methods or processes and apparatuses (e.g. electronic computing devices, such as a smartphone, PDA, etc.) for practicing those methods or processes; and, in the form of a computer program product having computer program code containing instructions embodied in non-transitory and/or tangible media, such as floppy diskettes, CD-ROMs, hard drives, USB (universal serial bus) drives, or any other machine readable storage medium, wherein, when the computer program code is loaded into and executed by a computer, the computer becomes an apparatus for practicing embodiments of the disclosed subject matter.

The various embodiments of the present disclosure may also be in the form of computer program code, for example, whether stored in a storage medium, loaded into and/or executed by a computer, or transmitted over some transmission medium, such as over electrical wiring or cabling, through fiber optics, or via electromagnetic radiation, wherein when the computer program code is loaded into and executed by a computer the computer becomes an apparatus for practicing embodiments of the disclosed subject matter. When implemented on a general-purpose microprocessor, the computer program code segments configure the microprocessor to create specific logic circuits. In some configurations, a set of computer-readable instructions stored on a computer-readable storage medium may be implemented by a general-purpose processor, which may transform the general-purpose processor or a device containing the general-purpose processor into a special-purpose device configured to implement or carry out the instructions.

The various embodiments may also be implemented using hardware that may include a processor, such as a general purpose microprocessor and/or an Application Specific Integrated Circuit (ASIC) that embodies all or part of the techniques according to embodiments of the disclosed subject matter in hardware and/or firmware. The processor may be coupled to memory, such as RAM, ROM, flash memory, a hard disk or any other device capable of storing digital information. The memory may store instructions adapted to be executed by the processor to perform the techniques according to embodiments of the disclosed subject matter.

BRIEF DESCRIPTION OF THE DRAWINGS

The above and other features, aspects, and advantages of the present disclosure will become better understood with regard to the following description, appended claims, and accompanying drawings where:

DETAILED DESCRIPTION

System Architecture

As disclosed herein, reference to "911" encompasses any emergency responder service, private and public, in any geographic location.

Network Based Service

Figure 1:
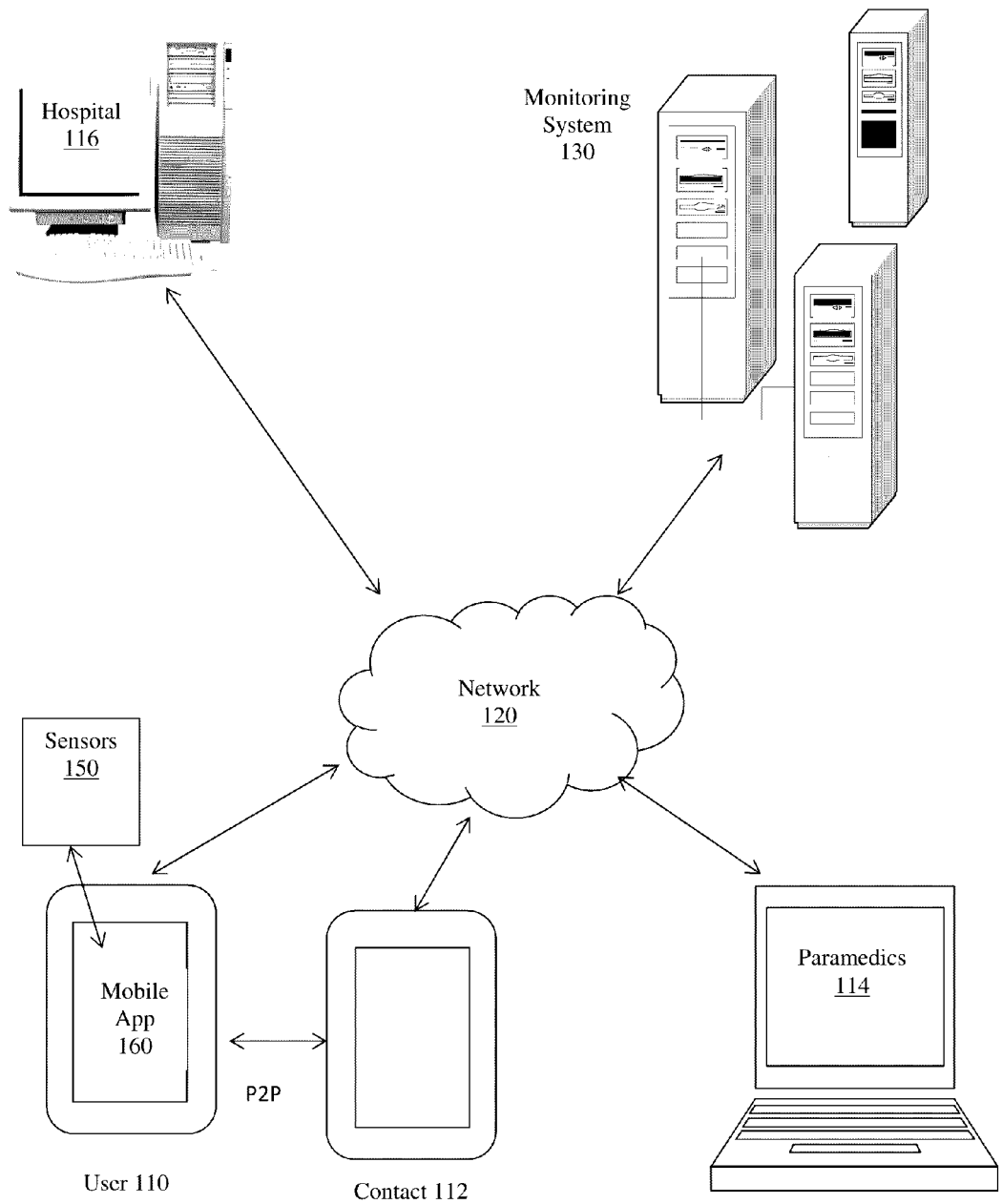
FIG. 1 is an illustration of one embodiment of the present invention comprising a networked based emergency responder service.

Embodiments of the presently disclosed subject matter may be implemented in and used with a variety of component and network architectures. As illustrated in FIG. 1, the system of the various embodiments may comprise, for example: one or more user (patient and or adult supervisor— e.g. adult child remotely monitoring senior citizen parent who is ill) electronic computing devices 110 communicating via a network 120 (e.g. the Internet) with the monitoring computer system 130 (server, database of user's records comprising medical and legal records, processor(s), network interface, etc.). The system may further comprise one or more of a user's contact(s) (family and friends) electronic computing devices 112 in communication with the system 130 via the network 120. The user-patient electronic computing devices 110 and their contact electronic computing devices 112 may also communicate directly via the network 120, and/or with remote servers, databases, cloud computing services and the like.

The system for various embodiment of the present disclosure may further comprise computer systems for emergency medical responders 114, such as the 911 responders (paramedics, fire department, etc.) and/or the hospital emergency room 116. System 114 may communicate directly with the server 130 to access the user's record, such as the user's medical record upon receipt of the user's "medical authorization code" and/or the user's legal record upon receipt of the user's "legal authorization code".

Figure 34:
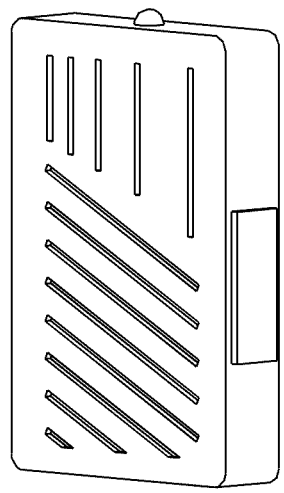
FIG. 34 is an illustration of a smoke and carbon monoxide detector.

The system may further comprise sensors 150 to enable the system to detect information about the user that is utilized by the system processor to carry out the steps disclosed herein. Sensors may comprise, for example: geographic location sensors (e.g. GPS tracking); fall detector/sensors of the user losing their balance and falling; medical equipment sensors to detect and analyze a user's vital signs, EKG, blood chemistry, medication that have taken or need to take. If a user has forgotten to turn on their phone and app, the system provides removable and wireless stick-anywhere emergency buttons strategically placed throughout the home and which when pushed, connects the user to the support center for assistance. The system also comprises an algorithm that allows users to turns on the phone and the app remotely to activate automated emergency alert. The system incorporates sensors/detectors for dangerous environments, such as smoke and carbon monoxide detectors which, when detected, automatically trigger an alert to the user and an automated emergency alert to emergency dispatchers depending of the amount present (see FIG. 34).

Figure 2:
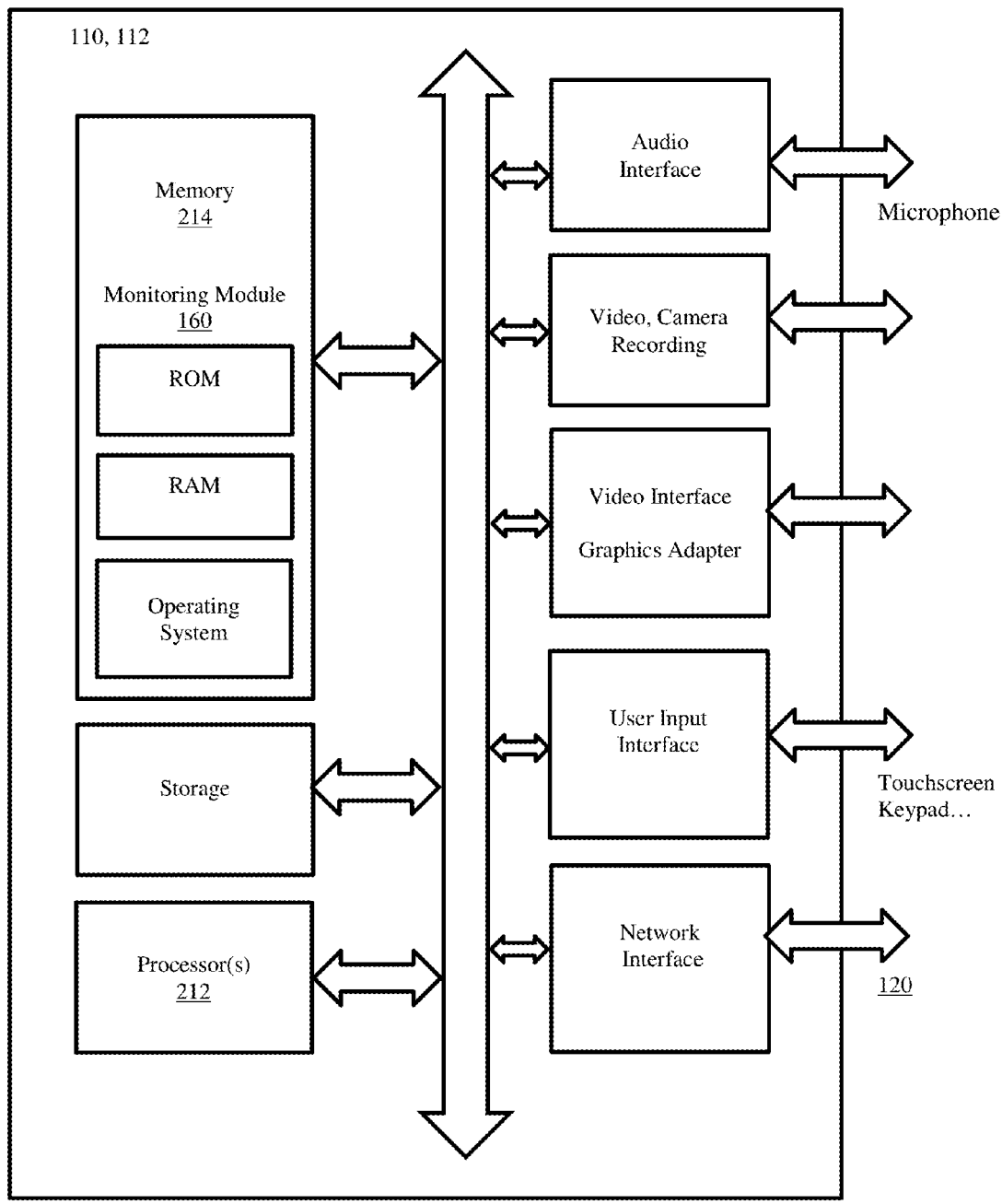
FIG. 2 is a block diagram of one exemplified user's electronic computing device utilizing the mobile app of the present invention.

The computer system may also comprise a separate application server storing the end-user application 160 (e.g. cloud computing), or the application 160 may be stored on the end-user's device 110 (see FIG. 2). Peer-to-peer computing between user computing device/apparatus 110 and contact's device/apparatus 112 enables the contact's (family and friends) electronic computing device 112 to communicate directly without interacting with the monitoring server 130. Therefore, the user can use a web application in lieu of the mobile app 160 to program their monitoring and rescue. Both types of applications can use a phone number or a combination of phone numbers, VoIP's, E911 and other means that are appropriate, adequate and compatible. Non-affiliated entities who do not have the system's white label application program interface (API) on their computer system, can access the system via its web-app or its other applications using the access/authorization code received to retrieve the related information (re: the user).

The server database may store users' computer records comprising one or more of: a user's medical records that are accessible to medical personnel with a medical authorization code provided by the server 130 (e.g. basic medical information within user's personal information folder and medical records within the medical haven/folder); a user's call list of contacts and their phone numbers, emails, a user's history of parameters selected for system automated activation of their call list and/or emergency responders; a history of their vital signs and symptoms monitored by medical equipment in communication with the server 130; legal records protected via a computer code and releasable with appropriate legal authority (e.g. court order for the monitoring server 130, the system's advanced communication center or its affiliates. to release the document specified in the court order e.g. deceased's last will and/or testament).

The Network 120 may comprise a local network, wide-area network, the Internet, or any other suitable communication network or networks, and may be implemented on any suitable platform including wired and/or wireless networks. The electronic computing devices 110, 112, 114, 116, may connect to the network 120 via a variety of methods such as a phone modem, wireless (cellular, satellite, microwave, infrared, radio, etc.) network, Local Area Network (LAN), Wide Area Network (WAN), or any such means as necessary to communicate to the monitoring server 130.

Call Center. The system may further comprise a "call center" (not shown) comprising a local or remote facility and/or web-based service for receiving user calls. The call center may also call the emergency responder dispatcher and disclose the relevant information in lieu of an automated call. The app customer support/communication center serves as a center for entities with a need to know to obtain information regarding a user (if the user pre-permitted it). For example, if an emergency was not called, then a code is not issued. However, if the user voluntarily goes to an emergency room or is hospitalized, then the hospital can contact the communication center and requests the user's information following established protocols or get it directly from the user (since the user has access), by issuing an access code which the hospital can use to access the user health records either through the system API they have installed in their computer system or via the system's web app if they are using the system API. Preferably, these health documents are read-only and non-modifiable. Corrected versions of the same documents can be added and the systems does not have the capabilities of deleting of modifying official documents to adhere to HIPAA. Hospitals and health professionals who wish to be a part of the system may do so via pre-registration.

When a 911 call is initiated, the support/communication center is notified and stays on guard/available to answer questions and help make the process smooth and seamless.

Users also have the option of phoning in to the support/ communication center for assistance with the app either directly from within the app, or from the phone that has the app installed, or by using any external means. Users can receive live help for setting up the app and navigating the app. They can give the app's technicians the command/ control of their screens/desktops for setup purposes and the technician would input the information provided by the user. They can call right from within the app or they can call from their personal telephone. Users also have the option of requesting that a live person plays the role of the app and checks on the user (as often as users choose). The live person will call/text/alert the user as requested respecting the exact intervals of time established by the user. The live person will follow and execute the user's wish/request/command to the letter and will do exactly as requested. All calls will be monitored for accuracy and the live person will observe "pre-emergency mode" and "emergency mode," just as the app would. This is to allow elderly or ill people, people who just prefer to not deal with electronics, or people who are not computer literate to use and fully benefit from the service.

No Internet Connection. To allow people to receive emergency help (with and without an Internet connection), the mobile app 160 by itself can carry out its basic function just from a working electronic computing device 110 (e.g. smartphone, cell phone) with no Internet connection. However, chatting, GPS location and other features that require an Internet connection with the mobile app 160 may not work without the Internet. In cases of no Internet connection, the user can establish a phone connection with the Live Communication Support Center; but the Communication Center may not be able to take control of the user's screen. The user may not be able to issue access/authorization codes without an Internet connection; but, they can access/print their medical records if they had stored them on their device 110 as well. All the functions work seamlessly when the system is connected to the Internet. The system may use the same Internet data plan that is used for email and web browsing or the phone's messaging or other means compatible and adequate. Of note, users can store their data both within the memory of device 110 and in the cloud. Storage in the device 110 allows users easy access to their files when they don't have an Internet connection, or when they travel to a country where Internet connection could be an issue. And, if there is no Internet connection, the system will use the residential address pre-entered by user in case of an emergency. The user is required to specify their exact location whenever they put the system on monitoring mode.

Mobile App 160

The computer program product houses a database of users/subscribers' information, and it is directly connected to the system server 130 that communicates with monitoring/support center(s). Users need an active subscription to be able to use the app 160. However, they may have non-restricted access to non-subscribers' areas where they can learn about the program, surf Q&A's, submit inquiries, subscribe to the app's newspaper, post in the blogging area, etc. Once downloaded, the software/app 160 displays a simple interface that is extremely user-friendly, interactive, intuitive and very easy to navigate. Main interface opens to other sub-interfaces. For example: "I need this for myself" or "I need this for a loved one."

FIG. 2 is a block diagram of one exemplified user's and contact's electronic computing device 110, 112 comprising satellite, and/or Internet-based telephone services, such as a cell phone, smartphone, PDA, laptop and tablet with voice over internet protocol service VoIP. In an exemplary embodiment, the user may setup their account and activate the Monitoring Mode using any device with Internet connectivity, such as their desktop computer. Using such a setup configuration, the system could automatically call their landline phone or cell phone (if lacking Internet service).

Device 110 includes a processing circuit comprising a processor 212, and a memory 214 that stores machine instructions that, when executed by the processor 212, causes the processor 212 to perform one or more of the operations and methods described herein. Processor 212 may optionally contain a cache memory unit for temporary local storage of instructions, data, or computer addresses. For example, using instructions retrieved from memory 214, the processor 212 may control the reception and manipulation of input and output data between components of the device 110. In various embodiments, the processor 212 can be implemented as a single-chip, multiple chips and/or other electrical components including one or more integrated circuits and printed circuit boards.

The processor 212 together with a suitable operating system may operate to execute instructions in the form of computer code and produce and use data. By way of example and not by way of limitation, the operating system may be Windows-based, Mac-based, or UNIX or Linux-based, among other suitable operating systems. Operating systems are generally well known and will not be described in further detail here.

Memory 214 encompasses one or more storage mediums and generally provides a place to store computer code (e.g., software and/or firmware) and data that are used by the device 110, 112. It may comprise, for example, electronic, optical, magnetic, or any other storage or transmission device capable of providing the processor 212 with program instructions. Memory 214 may further include a floppy disk, CD-ROM, DVD, magnetic disk, memory chip, ASIC, FPGA, EEPROM, EPROM, flash memory, optical media, or any other suitable memory from which processor 212 can read instructions in computer programming languages.

Memory 214 may include various other tangible, non-transitory computer-readable media including Read-Only Memory (ROM) and/or Random-Access Memory (RAM). As is well known in the art, ROM acts to transfer data and instructions uni-directionally to the processor 212, and RAM is used typically to transfer data and instructions in a bi-directional manner. In the various embodiments disclosed herein, RAM includes computer program instructions that when executed by the processor 212 cause the processor 212 to execute the Mobile App modules 160.

Processor 212 is generally coupled to a variety of interfaces such as graphics control (e.g. graphical processing unit (GPU)), video interface, audio interface, input interface, and other interfaces, such as camera hardware and software components housed within and/or connected to devices 110, 112 for recording and transmitting content. Processor 212 is also coupled to a network interface that allows the processor to be coupled to another computer or telecommunications network (e.g., the Internet). More particularly, the network interface generally allows processor 212 to receive information from and to output information to the network in the course of performing various method steps described in the embodiments herein.

Devices 110, 112 may further have installed within the device's memory computer instructions for executing the various embodiments of the disclosure comprising a native application, a web application, or a widget type application to carry out the methods of the embodiments disclosed herein. In a preferred embodiment, a native application (e.g. computer program product) is installed on the device, wherein it is either pre-installed on the device or it is downloaded from the Internet via email and activated with a code generated by the system server. It may be written in a language to run on a variety of different types of devices; or it may be written in a device-specific computer programming language for a specific type of device.

In another embodiment, a web application resides on a remote server accessed via a network. The web application performs basically all the same task as a native application, usually by downloading part of the application to the end user's device 110, 112 for local processing each time it is used. The web application software is written as Web pages in HTML and CSS or other language(s) serving the same purpose, with the interactive parts in JavaScript or other language(s). Alternatively, the web application can comprise a widget as a packaged/downloadable/installable web application; making it more like a traditional application than a web application; but like a web application uses HTML/CSS/JavaScript and access to the Internet. The device 110, 112 may include a web browser running applications (e.g. Java applets or other like applications), comprising application programming interfaces ("APIs") to other software applications running on remote servers that provide, for example, cloud based services and comment posting.

Cellular Telephone Capacity—no Internet. In addition to Internet connectivity, the electronic computing devices 110, 114, may also communicate with the server 130 via a network 120 comprising radio wave transmission components dedicated to cellular telephone functions. The basic components shown provide the ability for the mobile computing device to perform radio-frequency communications, including telephonic communications. The radio components include a baseband-radio processor, an RF transceiver module, a radio flash memory, and an antenna.

The transceiver module may comprise two separate components for transmitting and receiving signals, or a single component for both transmitting and receiving signals. The receiver portion of the transceiver module communicatively couples with a radio signal input of the user's electronic computing device 110 antenna. The antenna receives communication signals that are processed by the radio processor for output through the speaker. The transmitter portion of the transceiver communicatively couples a radio signal output of the device 110 to the antenna, where communication signals are transmitted via radio waves to an established call. The communication signals for the transmission comprises voice (e.g., received through the microphone of the device 110) that is processed by the radio processor for transmission through the transmitter of the transceiver to the established call.

In one embodiment, communications using the described radio communications may be over a voice or data network. Examples of voice networks include Global System of Mobile (GSM) communication system, a Code Division, Multiple Access (CDMA system), and a Universal Mobile Telecommunications System (UMTS). Examples of data networks include General Packet Radio Service (GPRS), third-generation (3G) mobile, High Speed Download Packet Access (HSDPA), High Speed Uplink Packet Access (HSUPA), and Worldwide Interoperability for Microwave Access (WiMAX).

While other components may be provided with the radio subsystem, the basic components shown provide the ability for the user's electronic computing device to perform radio-frequency communications, including telephonic communications. In an exemplary embodiment, many, if not all, of the components under the control of the central processor are not required by the radio subsystem when a telephone call is established (e.g., connected or ongoing). The radio processor may communicate with central processor using a serial line.

Novel Smartphone

Figure 8:
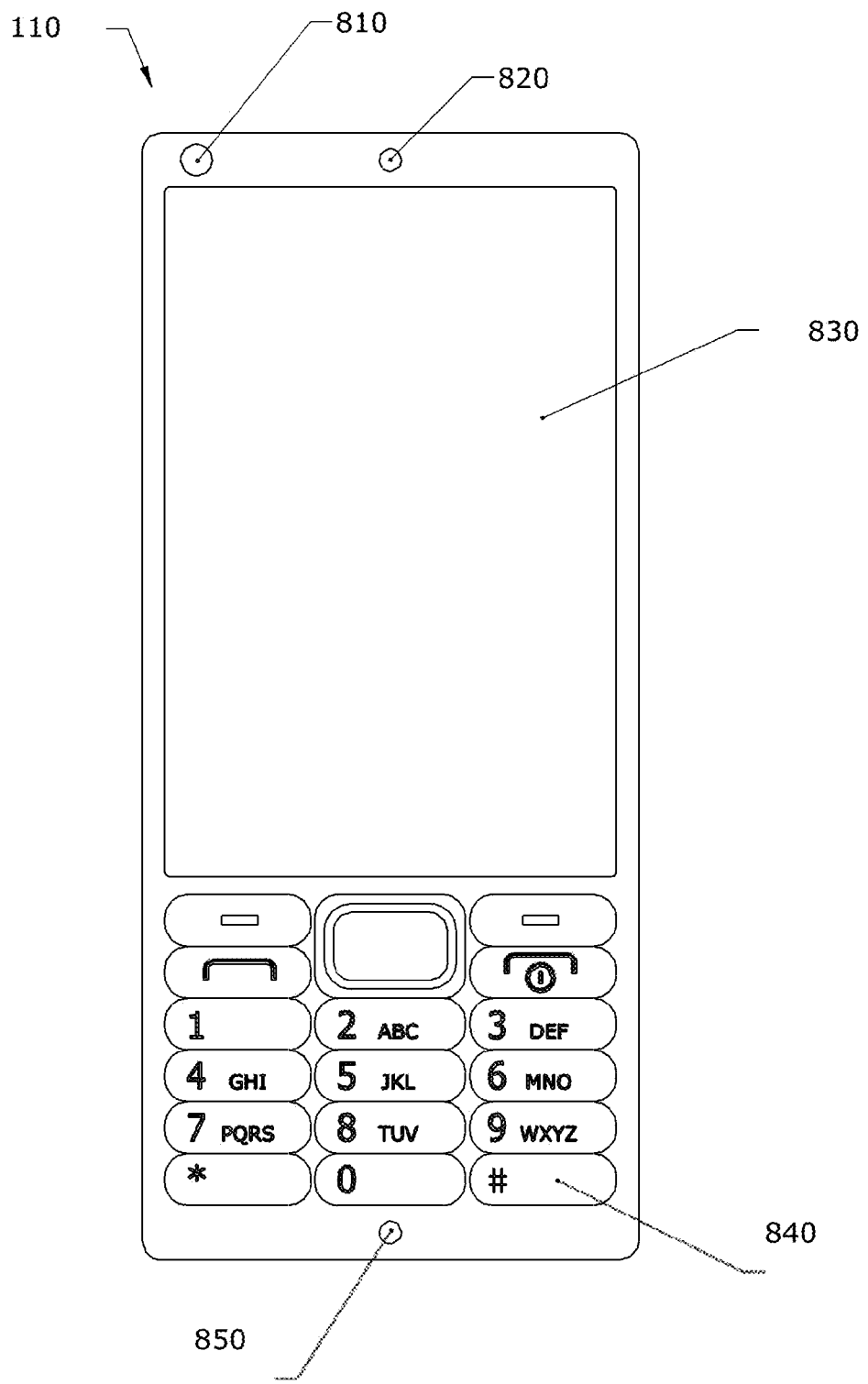
FIGS. 8-14 illustrate various views of a novel smartphone having the mobile application of the present invention installed thereon, or the functionality accessible via the network, in accordance with the present invention.
Figure 9:
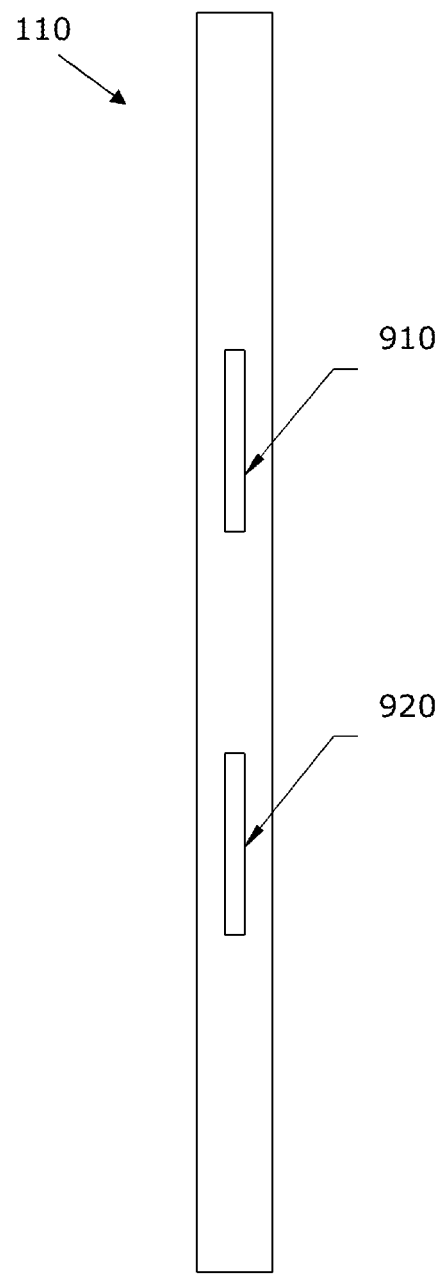
Figure 10:
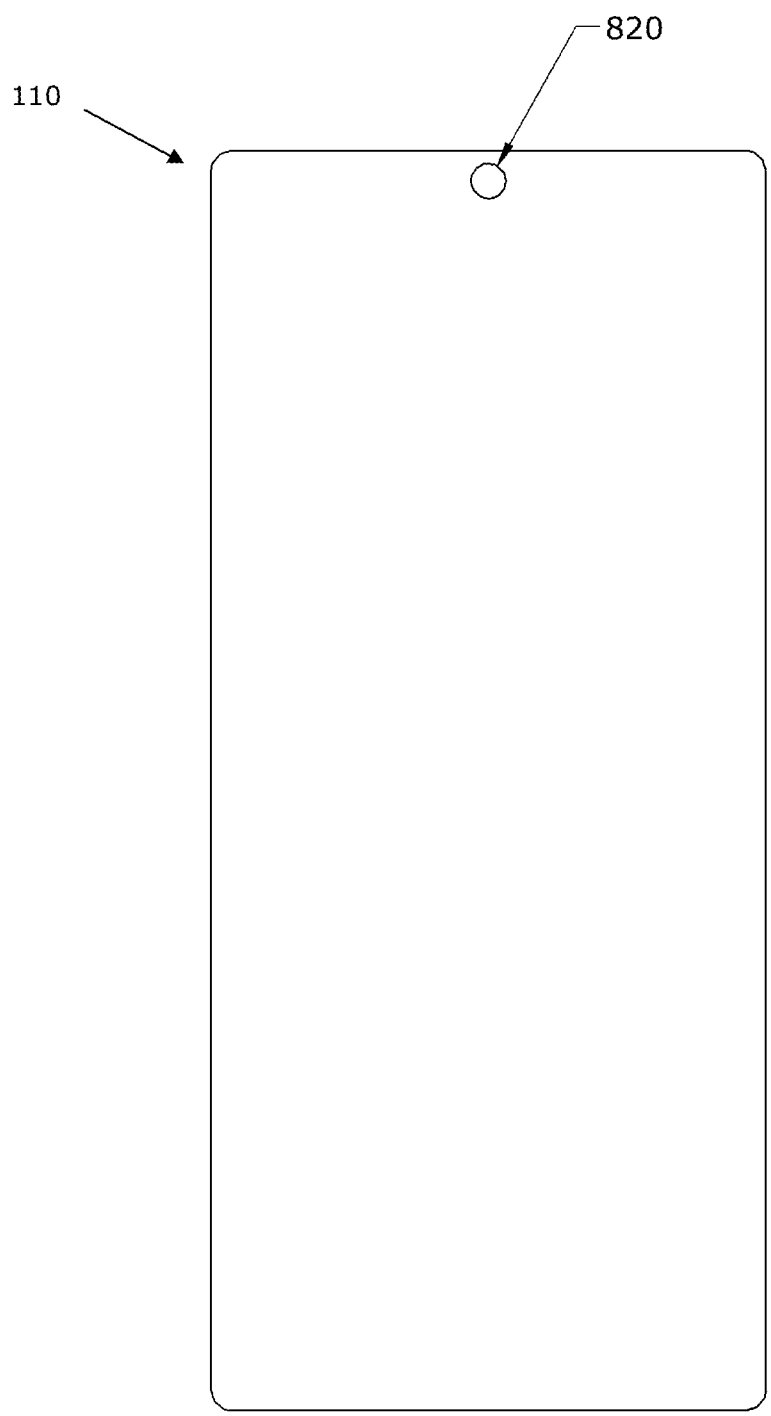
Figure 11:
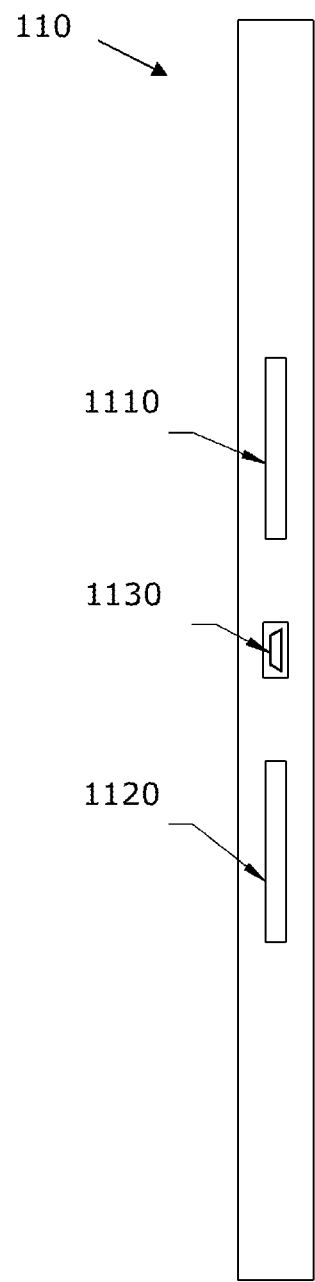
Figure 12:
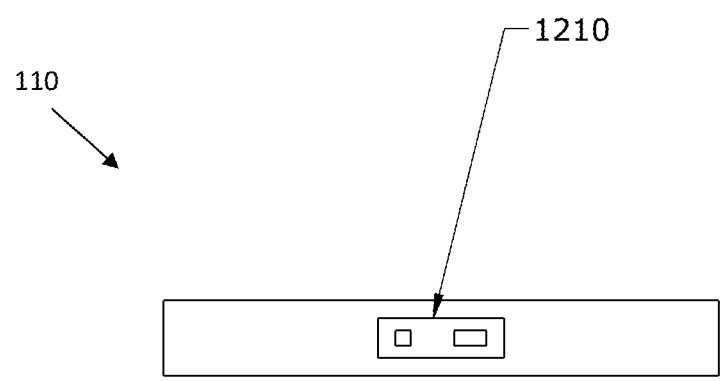
Figure 13:
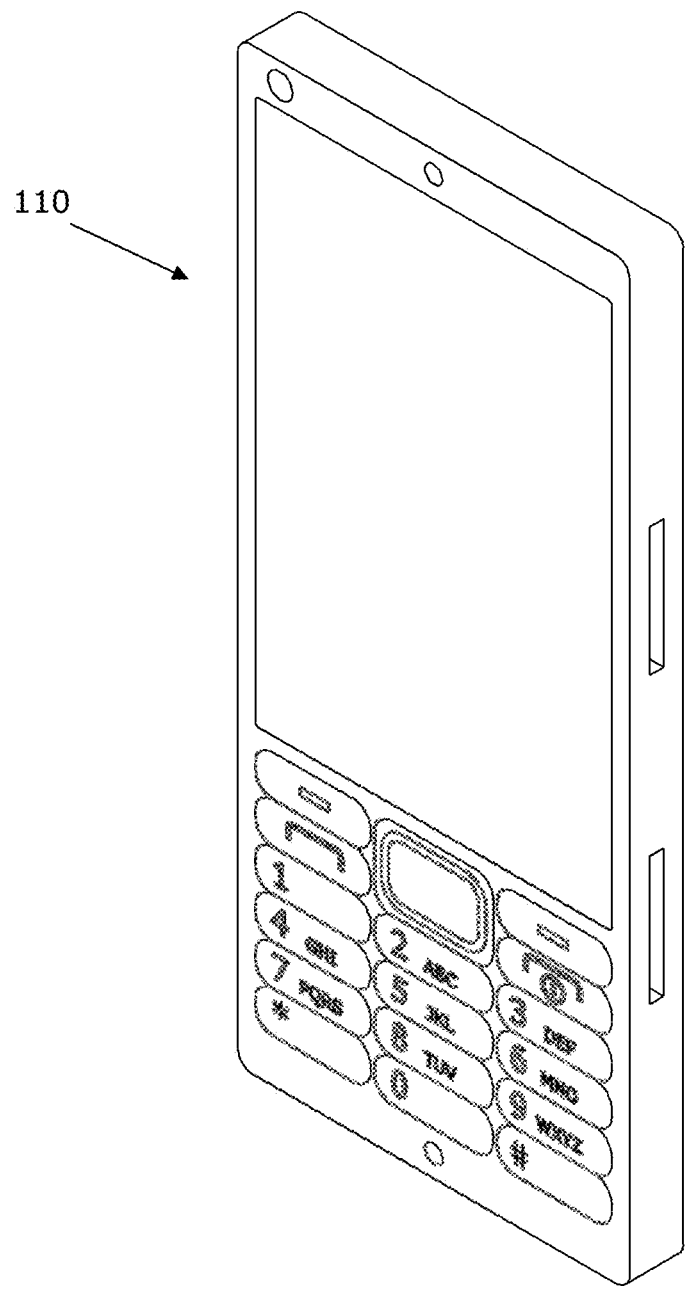
Figure 14:
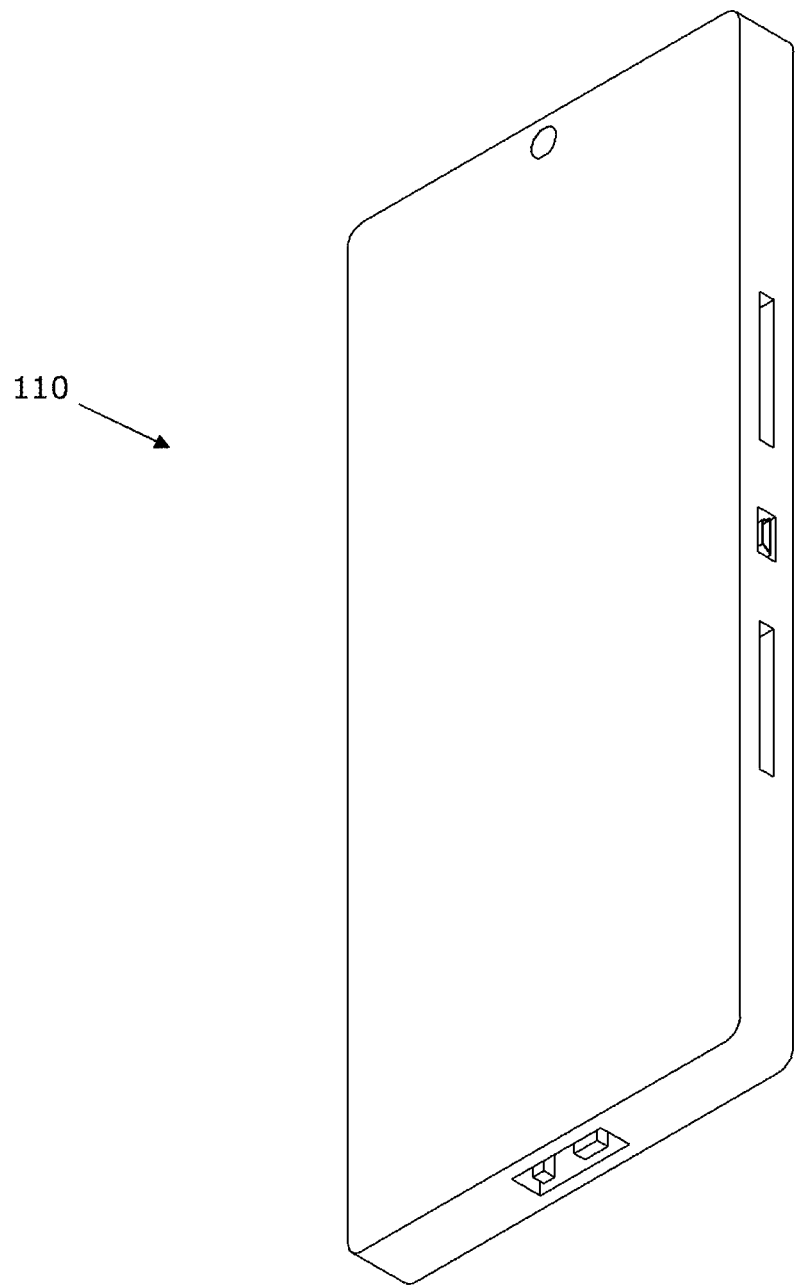
Figure 33:
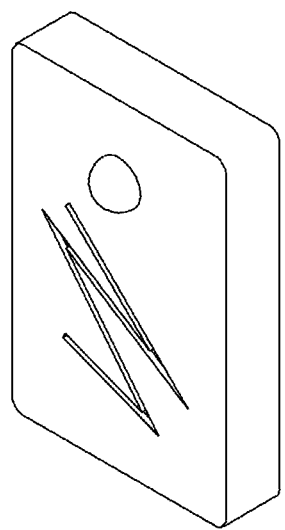
Figure 52:
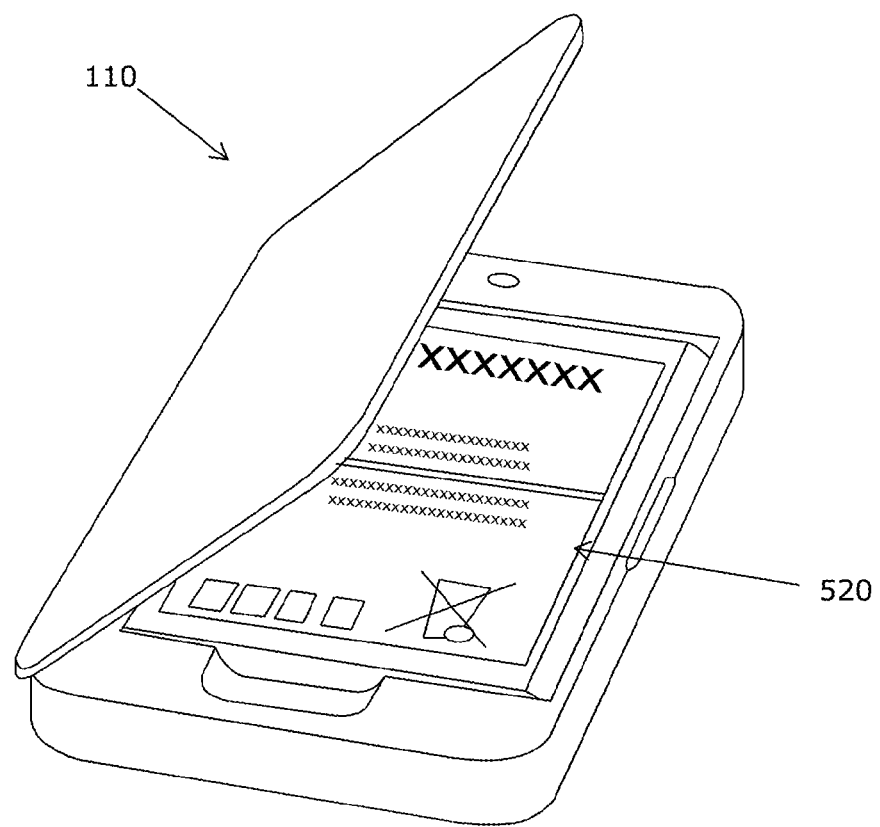
FIGS. 52 and 53 are views of one embodiment of a replaceable battery for a smartphone; and, FIG. 54 is an illustration of a smart watch in the present invention.
Figure 53:
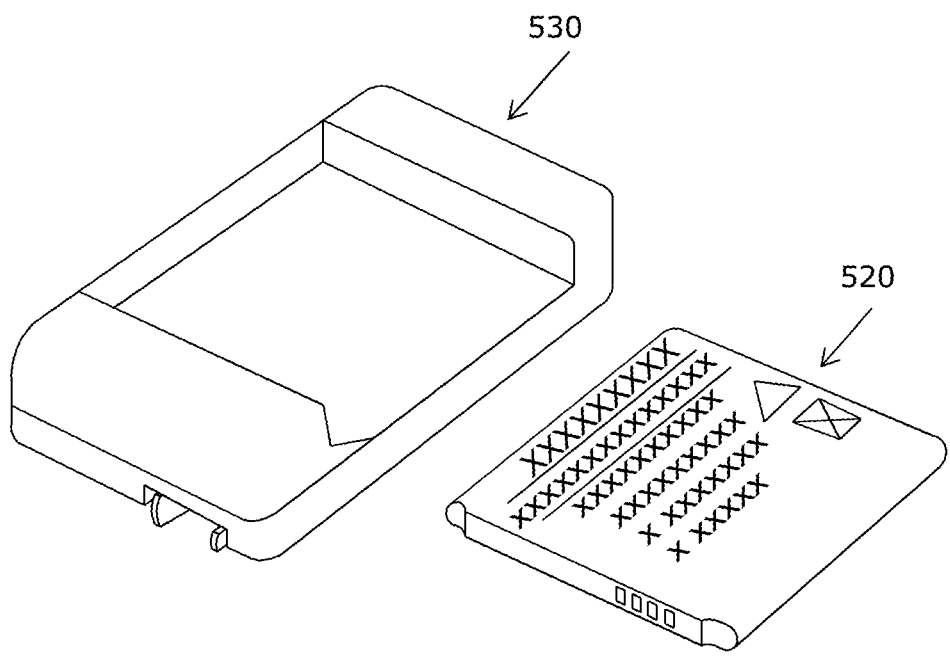

The present invention comprises one or more novel user electronic computing devices 110, such as smartphones with a long battery life and/or chargeable and replaceable battery (see FIG. 52, 53; battery 520, charger 530), and/or with a fall detector (FIG. 33), smoke detector (FIG. 34), and the ability to track a user's health vital signs (e.g. FIG. 39, EKG monitoring, etc.), as shown in FIGS. 8-14. FIG. 8 is a front view of the smartphone of the present invention comprising: front screen 810; a speaker 820; a screen 830; a keyboard 840, and a microphone 850. FIG. 9 is a right side view with two slots 910, 920. FIG. 10 is a rear view with speaker 820. FIG. 11 is a left side view with slots 1110, 1120, and cable connector slot 1130. FIG. 12 is a bottom view with the charger slot 1210. FIG. 13 is a front, right perspective view, and FIG. 14 is a rear, left perspective view.

Figure 31:
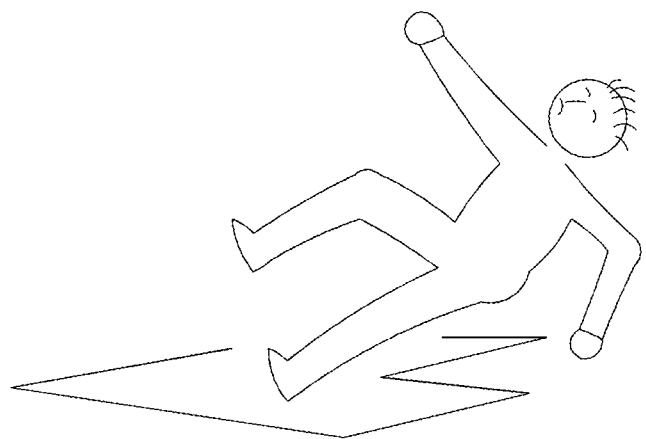
FIGS. 31-33 illustrate methods of falling and a fall detector device.
Figure 32:
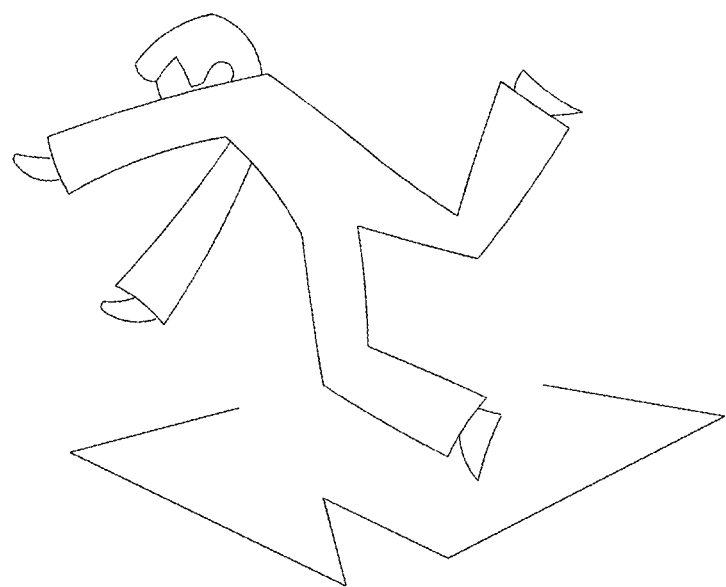
Figure 37:
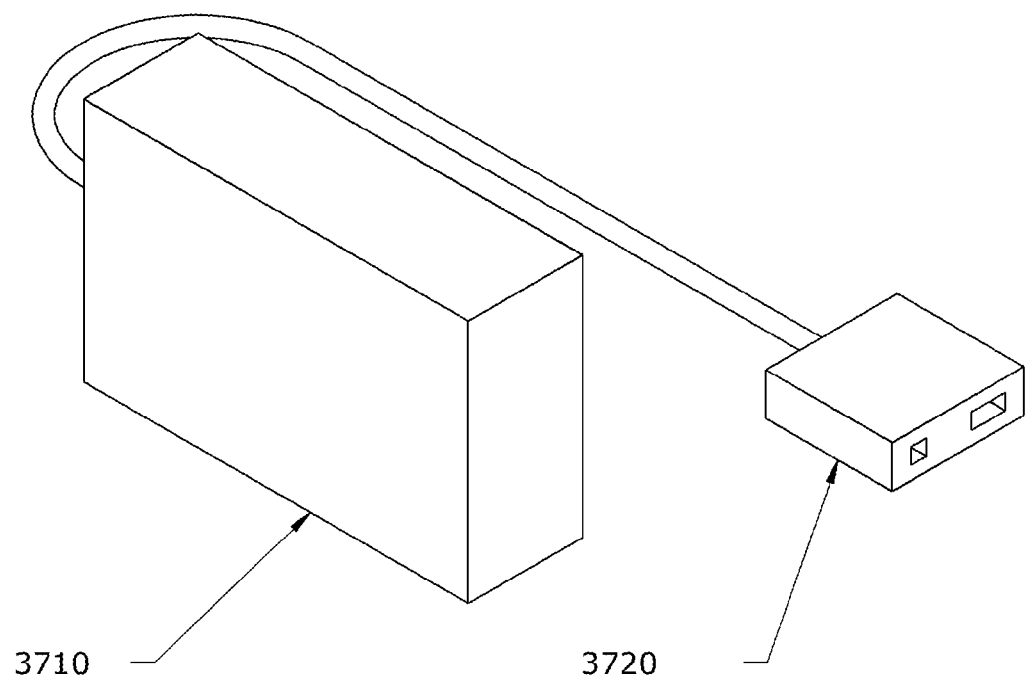
FIG. 37 illustrates an external battery for use with the present invention.
Figure 38:
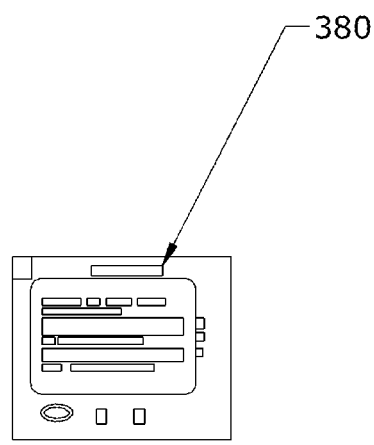
FIG. 38 illustrates a SIM card for use with the smartphone of the present invention.

For example, device 110 may comprise an all-in-one stand-alone smartphone supporting three or more of the following global communication technologies: GSM, CDMA, GPRS, EDGE, UMTS, HSDPA, HSUPA, HSPA+, TD-LTE, FD-LTE, CDMA, EV-DO, LTE and others that can work with most wireless service providers and Internet connectors utilizing one or more of the following: 802.11/Wi-Fi/WiMAX/Mi-Fi/Z-wave etc. The device also integrates a long-life battery (e.g. FIG. 37 with external battery 3710 with connector 3720), a GPS, accelerometers, inclinometers, a gyroscope, fall detector sensors (e.g. FIGS. 31-33), life signs sensors, with and without M2M technology EKGs and lab sensors.

Account Setup

If a computer and/or mobile electronic computing device does not come preloaded with the cross-platform and/or native software/app, the user may download it into their computers or mobile electronic computing devices. The user registers with the system 130 by following the prompt and/or answering a few questions regarding their health, current treatments, their emergency contacts, their support system etc., and by giving specific orders' execution at specific intervals, and also by providing advance directives to the app on the following.

Information the user may input may include: (i) how to proceed or initiate a request for help who to call/text/alert for what; (ii) when to call/text/alert; (iii) what to tell potential or actual rescuer(s); (iv) what is to be kept confidential; (v) who to inform and who not to inform; who is allowed to act on user's behalf and who is not; (vii) who can visit the user at the hospital and who cannot; and (viii) what the user wants the rescuer(s) to do for whom or what. Users can create a code that responds/pairs up with an order. The computer system allows users to program a preset combination of keys letters and/or numbers and whenever the user types in the combination created, the system will work silently and unnoticeably in the background while the user's phone is showing a totally normal screen, so offenders are totally unaware of the system working to save the user. For example, the code "1756" could mean "call 911 immediately and pass on a specific preset message," in which case the system would activate its emergency mode and delivers the preset message to the emergency authorities. The system can act as a voice-activated secret agent by allowing users to program their own voice recognized one-word request or a combination of words, letters and/or numbers or a full sentence to activate the monitoring, pre-emergency or emergency mode. For example, if users find themselves in a situation where they are able to only say one word, they may program the system to recognize the meaning of them stating "HELP NOW," or its equivalents, as indicating a specific urgency. For example, if a user states "Mom, I am fine," it might mean he is being robbed or kidnapped, and the system will activate emergency mode linked to this urgency. And if turns out it was a false alarm, the user will be allowed to abort. Users can also setup their own gestures and the gestures meaning for the app. For example, a swap from right to left on the screen means that the app must perform such and such action, whereas a swap from left to right may means something else. It's all up to the user. A finger swap diagonally could mean text this preset message to a specific person. The user creates the condition and what needs to be done. Every user has the freedom to create their own unlimited codes or gestures, putting the systems in stealth mode recording/functioning discreetly.

Overview of the Monitoring, Pre-Emergency, and Emergency Mode

Figure 3:
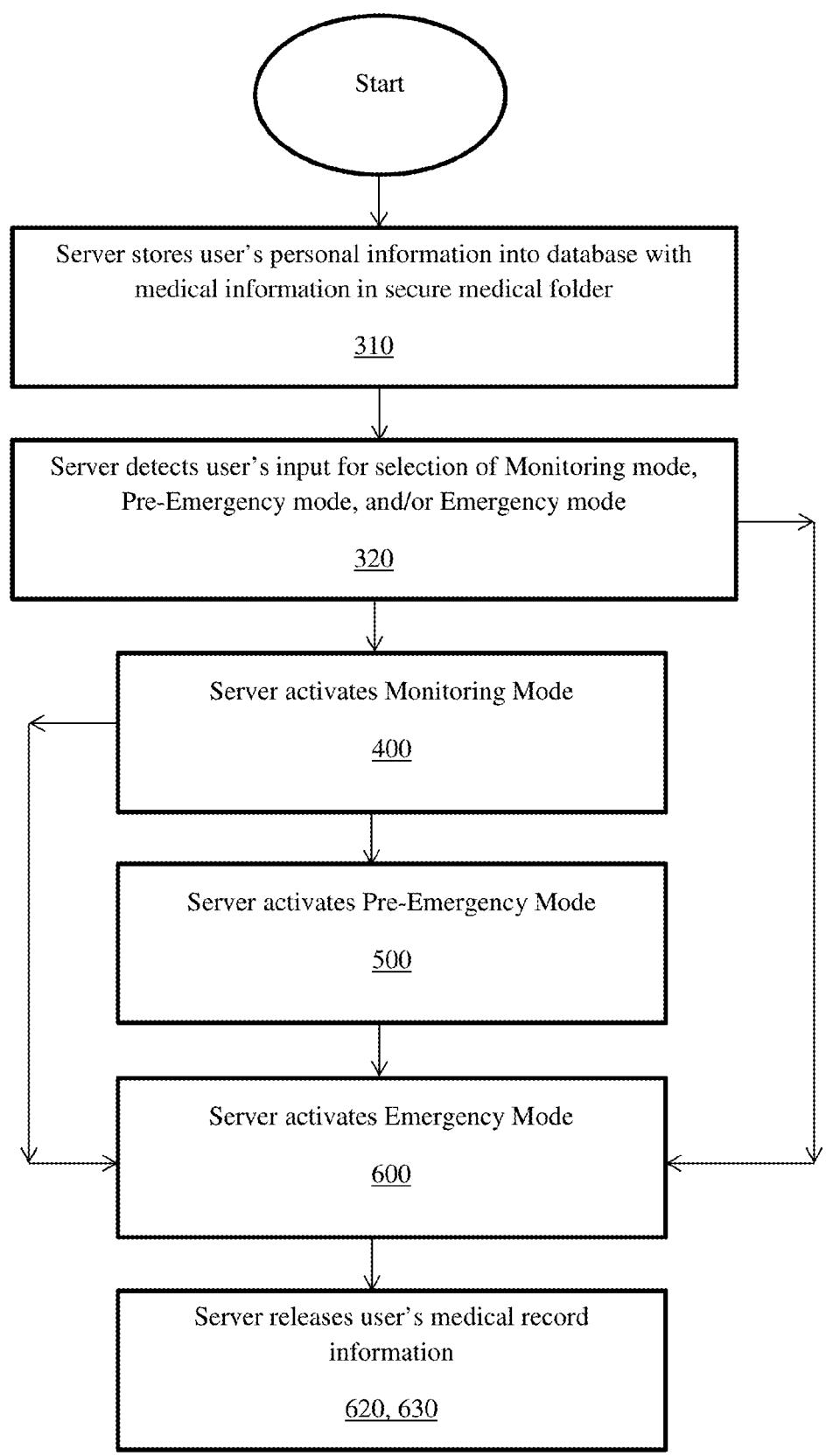
FIG. 3 is a flowchart of the primary steps in the various embodiments in accordance with the user's selections, including Monitoring, Pre-Emergency and/or Emergency modes.

FIG. 3 is a high level flowchart of the computer system steps in response to user input for selecting one or more modes comprising the Monitoring 400, Pre-Emergency 500 and/or Emergency Mode 600.

The computer system 130 intuitively detects medical conditions' patterns and monitors patient accordingly by periodically polling the individual through a telephone call (or text message) to make sure that they are OK and not in need of assistance. If the individual fails to respond to this poll, the computer system 130 will proceed to either call a preprogrammed list of relatives or friends to notify them of a potential emergency situation or call the appropriate emergency number (911 for USA) if the user has requested it. When the steps include calling a list of relatives or friends, the computer system will immediately notify 911 or the emergency number applicable (for other countries) regarding a potential emergency when the list is exhausted. In some cases, if desired or if required, it can also contact 911 directly without calling any other emergency contacts.

In step 310, the computer system (c. s.) database (i.e. user's phone or remote server) stores the user's personal information, in text and/or speech form or any other compatible form, such as names, exact location/addresses (both current/real time and permanent), emergency contacts, corresponding language, phone numbers, preferred method of transfer (text-to-speech, text-to-text, speech-to-text, speech-to-speech, voice-recognition, etc., according to user's choice or the system's automated choice if user did not make a choice), messages to be potentially transmitted to emergency contacts listed, and confidential and non-confidential messages (including basic medical information, current vital signs and other labs and access code to file/medical folder containing the medical records) to be potentially transmitted to 911 receptionist. Messages to 911 may be delivered in speech form exclusively and/or via text messaging, instant messaging, etc. or whatever means a user's emergency responder service provides for receiving emergency calls.

The computer system detects the user's confidential information that is to be included in the user's (confidential) medical folder. The user can even elect to have his/her doctor input the important medical information or an entire medical chart etc. This folder is accessible through a rigid authentication that may include but is not limited to: Generated Code, combination of fingerprint, iris or facial recognition plus password plus site key identification and PIN.

In step 320, the computer system integrates multiple modes (i.e. Monitoring Mode 400, Pre-emergency Mode 500 (where emergency contacts listed are contacted per user's order of priority), Emergency Mode 600 (where 911 is called)) in response to the user's inputted selection of the modes. The user may select to bypass mode 400 and/or 500 and activate only the Emergency Mode 600 if they fail to call back. The computer system detects mode(s), order of modes, mode(s) to bypass (if any) etc. requested by user.

The user has the choice of indicating what they feel is the issue or the source of malaise along with signs and symptoms and an explanation of the risky activity the user is about to do. Telling the app that they don't feel so well or that they are about to proceed with a risky activity can be done manually, vocally or by using any other sensor input enabled by the user's computing devices or any other means appropriate.

Also, the system can be used to monitor multiple users and a user or someone acting on behalf of a user, such as a caregiver or a daughter having the system remotely monitoring her mother, is able to set the amount of time they want monitoring. At the end of preset/set time, the user has the choice of letting the app continue monitoring as per the chosen interval. Users can use alternate telephones to receive incoming calls from the app. They can also sign up for an extra phone number if they like. Users may use one or multiple other personal phones or any phones (home phone, cell phones, VoIP, internet phone and any other phones) as call-to receiving phones meaning other phones that do not have the system installed on them. It can be used via a single mobile device or computer or it can be used via multiple phone devices. The user may decide if they want a ring tone, a buzz, an alarm sound like tone or any other alerting means that produce the same result.

For example: if Modes 400, 500, and 600 are selected by the user, then the computer system would first monitor the user {calling user within the time sequence requested this is the call back for example, user would select "monitor me for one hour", "call me back every five minutes", if I don't answer, call me back every 30 seconds or in 30 seconds for 2 minutes while also calling my emergency contacts, if there is no answer at the end of the 2 minutes.

Monitoring Mode

Figure 4:
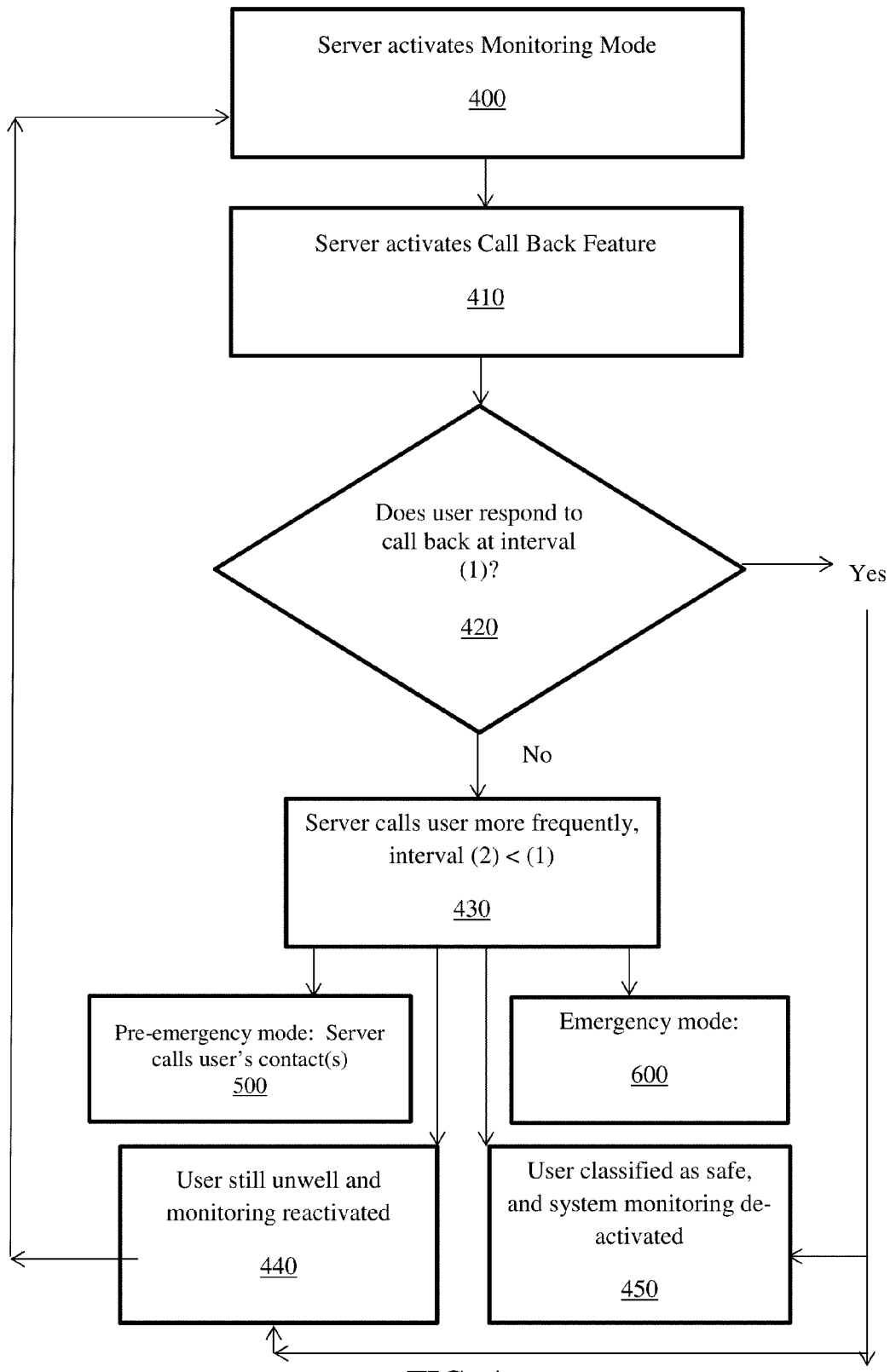
FIG. 4 is a flowchart of computer steps during the Monitoring Mode.

FIG. 4 is a flowchart of the general computer steps for the Monitoring mode 400. In step 410, the computer system activates the "call back" feature in response to the user's input. The user's input comprises selection of a variety of data input, such as:

a) System 130 detects user's requested time sequence of calls to be made (for example, computer system to call emergency contact within three minutes of user not answering—call 911 within five minutes of user not answering or in two minutes of emergency contacts not answering etc.) and duration of session (for example: overall monitoring to last 2 hours).

b) System 130 detects when, how, who, in what case, in what order to do this or that, or to call who or what etc.

c) The system 130 detects responses and/or request received by emergency contact(s) and is able to establish chat and/or conference call between user and emergency contacts or between emergency contact(s). The system allows the end receiver to choose to either answer, not answer, or forward call to another number or emergency contact(s), or invite others people to the conversation etc.

In step 420, the system 130 determines if user responds to the call back at time interval t(1) (time setup by user or by system based on user's medical condition). If yes, then user can indicate that they still feel unwell and continue the monitoring (step 440); or, that they are fine, and cease the monitoring (step 450).

In step 430, system 130 calls the user more frequently (interval (2)<(1)) if the user did not respond within time interval t(1), wherein steps 440 and 450 are activated if the user answers the call and indicates that they do not need an ambulance.

In step 440, the computer system 130 detects selection(s) to be renewed/repeated at the end of a session. For example, a session ends with user not feeling in immediate need of emergency rescue and therefore answered all the automated calls generated by c. s. (which as a result stopped the process of calling 911), but if the user is still not feeling well and wants more monitoring, the user can ask the system to repeat his/her previous selections whatever they were and/or modify his/her previous selection or start a brand new session. For example, if Jane had set up the system for Monitoring and Emergency modes (e.g. bypass Pre-emergency mode to call contacts), and if Jane wants to repeat that same process at the end of her session, Jane instructs the system to repeat selection.

In step 450, the system 130 stops the monitoring and automated call back mode if the user answers and indicates that they are fine. The automated voice system can detect if the user states they need medical assistance. The system 130 also detects a user or automated request to stop a monitoring session, stop a specific mode, change mode, change time sequence, etc.

In step 500, the system 130 detects that the user is not responding, and activates the user's call list of contacts if: 1) the user setup the Monitoring Mode for this (versus calling 911 directly); and, 2) if the system determines that the user's medical history and condition does not require calling 911 immediately. (See FIG. 5, Pre-emergency Mode).

In step 600, FIG. 4, the computer system 130 detects which symptoms (from user's inputted symptoms) require bypassing the Pre-emergency mode and switch directly to calling 911 if there is no response from the user within the preset interval. (See FIG. 6, Emergency Mode). For example, in bypassing the Pre-emergency mode, the system 130 can also intuitively, depending on user's current health conditions, health history and as well as sickness patterns, and real-time data on the user's medical stats (e.g. vital signs, etc.), elect to bypass the user's request of calling emergency contact(s) and call 911 directly if both actions cannot take place simultaneously depending on software or device restrictions. If so, then the system notifies the user's emergency contacts after calling (911 for USA) emergency professionals. If a device allows both actions to take place at the same time, then both 911 and emergency contacts can be alerted simultaneously. If the user is not responding to a computer system automated phone call, this situation triggers an automated emergency call (e.g. 911 for USA), wherein the system transmits a code protecting the user's medical records on the system database (if there is one), reason for the emergency call, a brief health info to the dispatcher/receptionist, if pet and/or child and/or other dependent care is required, etc. The system is able to self-switch to auto-silent and auto-pilot if a situation requires it based on input from the user as reason for requesting monitoring.

Pre-Emergency Mode

The Pre-Emergency Mode gives the user's contact emergencies the ability to ask the app to call/text/alert an alternate emergency of their own. For example, Jessica is not feeling so well and decide to put the app on "Monitoring mode." She had listed her friend Michelle as her first emergency contact. She becomes dizzier and unable to answer the phone. The app senses a problem and therefore switches to "Pre-emergency mode" and calls/texts/alerts Michelle who is unfortunately currently out of state or at work. Michelle receives the call/text/alert and forwards the request to her husband David and/or asks the app to call/text/alert David, who just happens to be not too far from Jessica's apartment, to go and help her. David hurries to Jessica's location to help her thanks to this app. This is an immediate plan.

Figure 5:
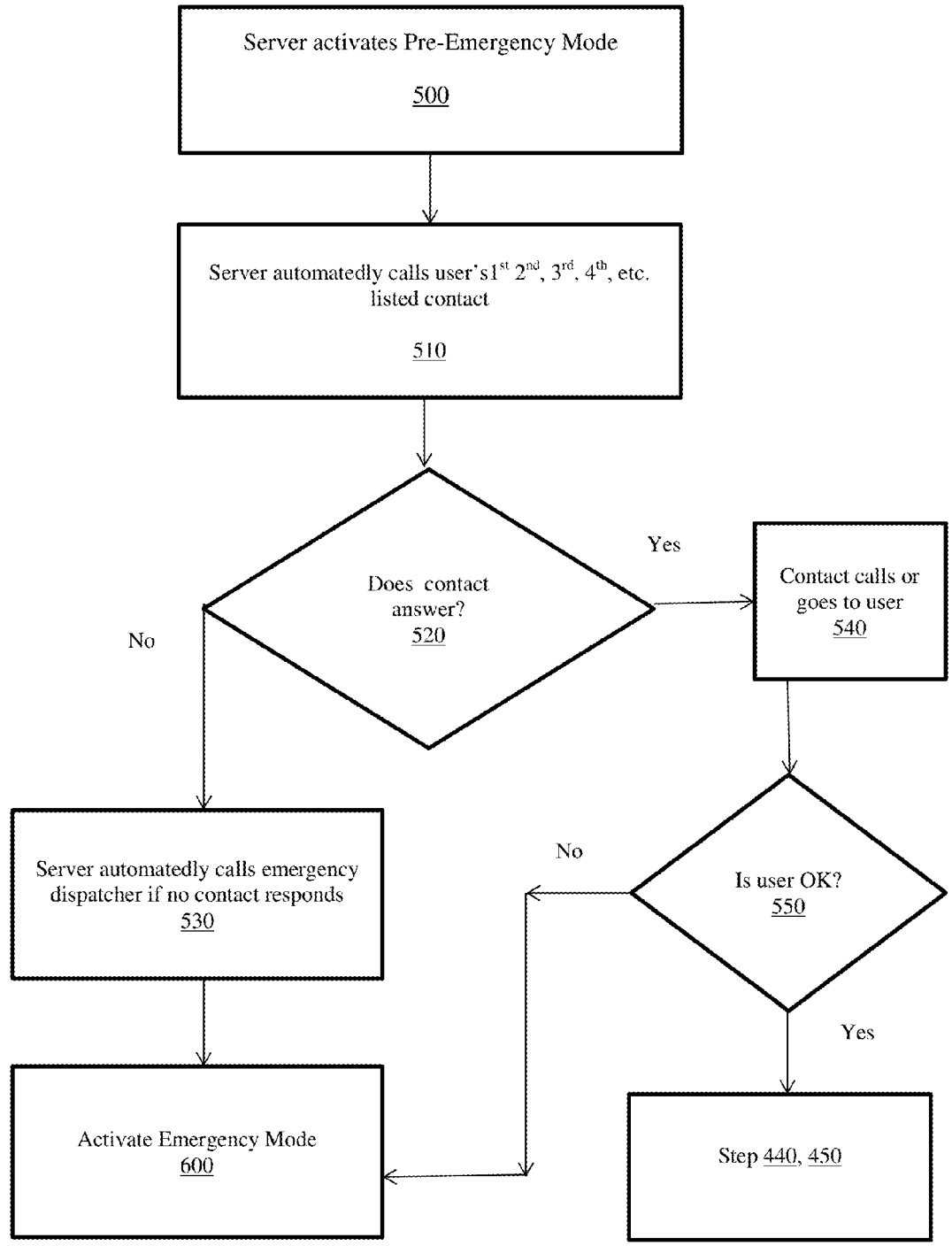
FIG. 5 is a flowchart of computer steps during the Pre-Emergency Mode.

FIG. 5 is a flowchart of the computer steps for the Pre-Emergency Mode 500. The computer system calls the user's emergency contacts listed depending on the user's request and severity of illness (i.e. symptoms recorded by the user, fragility of the user's real-time situation, etc.). For example, the user may request that emergency contacts are contacted but the computer system can either bypass that request to call 911, or the like, directly first and then call the emergency contact afterwards if a symptom listed by the user requires that action (i.e. upon user not answering automated call).

In step 510, the system detects that the user is not responding in the time interval set up in step 410 (e.g. t(1)), and activates the user's emergency contact list (e.g. family, friends, neighbor, etc.) stored in their record on the system database.

In step 520, the system detects if the user's contact answers the call and/or if a set time has passed. For example, the system may go down the list of user's contacts, but no one answers the call because they are not available (e.g. middle of night and phones are off or in another room), then the system activate the Emergency Mode 600 (step 530). And/or the user may have setup the Monitoring mode in step 410 that if a specific time period had passed (e.g. t(2) or another time period t(3)) and the system could not reach a contact, then to activate the Emergency Mode 600.

In step 540, a user's contact answers the system call, and the system automatedly tells the contact to either call or go over to the user's location. The system may also provide the location if this feature is enabled on the user's device 110, otherwise it is assumed that the user is at their home.

In step 550, the contact determines if the user is alright by talking to them, video chatting with them, or physically seeing them in person. If the contact determines that they are not alright, they may call emergency responders themselves, or ask the system 130 to automatedly activate the Emergency Mode 600 right from their screen. If the contact alternatively determines that they are alright, they may then elect to continue, reactivate and keep the parameters of the user's input or change them (step 440); and/or to stop the monitoring (step 450). The contact may also choose to ignore the system by not responding to the call or text which action either automatically switches to calling the next emergency contact or switch the system to Emergency mode.

Emergency Mode

Figure 6:
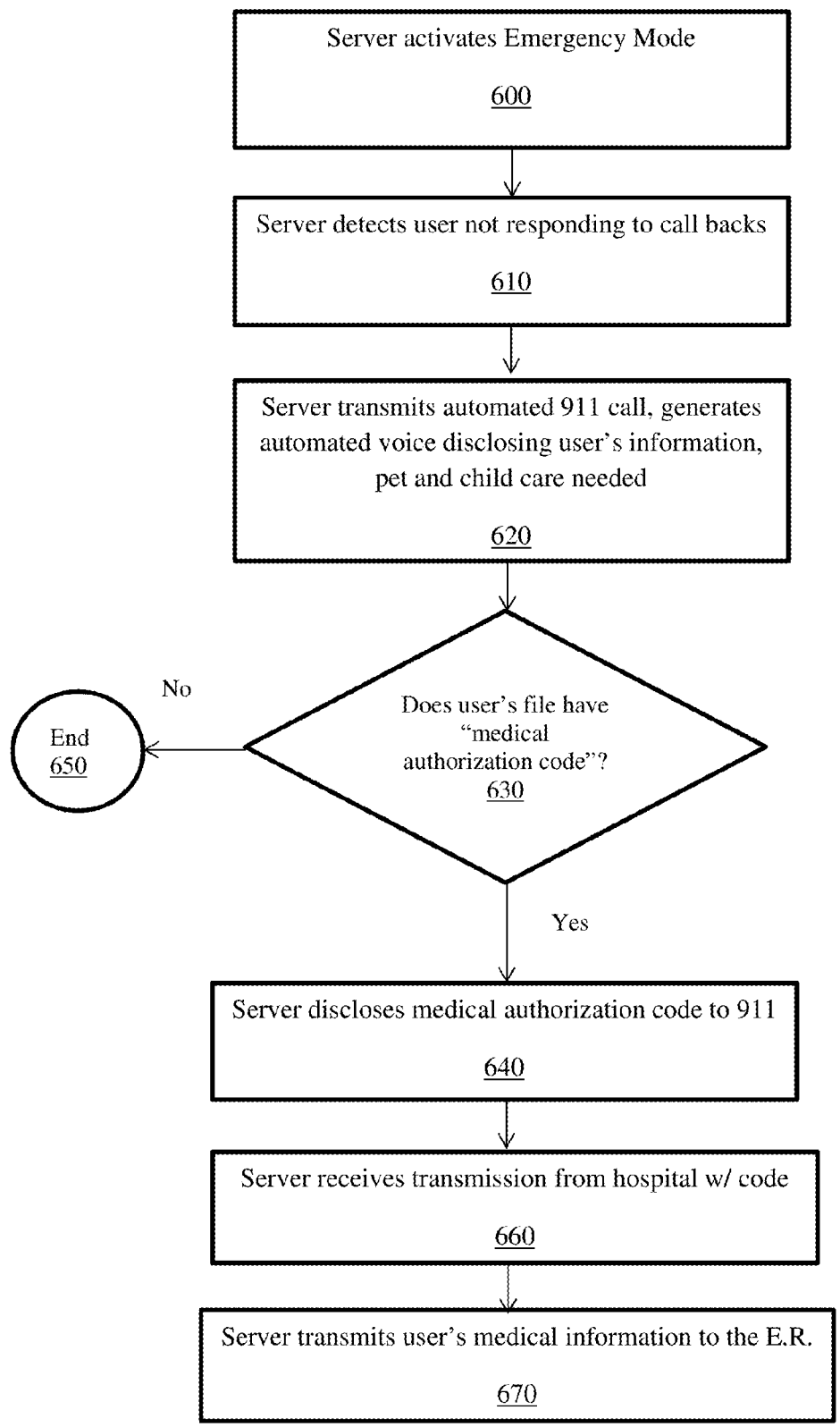
FIG. 6 is a flowchart of computer steps during the Emergency Mode.

FIG. 6 is a flowchart of the computer steps for the Emergency Mode 600, either selected initially by the user, thus bypassing the Monitoring Mode 400 and the Pre-Emergency Mode 500, otherwise known herein as the "no call back" feature; or, as a result of the Monitoring Mode 400 and/or the Pre-Emergency Mode 500 indicating that the user is not responding to the "call back" feature, and can be presumed to be incapacitated requiring emergency responders being sent to their location. This system mimics the same actions usually taken in a hospital setting when a patient becomes unresponsive and emergency help is therefore activated.

No Call Back. If only the Emergency Mode is selected, system 130 will proceed to calling emergency responders immediately or within the specified time frame (for example in one to two minutes, as requested by user or intuitively determined by the system without monitoring first). This option is appropriate if the user feels the impending doom of being about to pass out and does not want to delay rescue. That delayed option gives the user a limited time to stop the 911 call if it becomes necessary (such as if user thought s/he was about to pass out but did not pass out and is feeling more or less OK).

In step 610, the computer system detects that the user is not responding to the phone call; and, in step 620, it triggers an automated 911 call to notify emergency responders of a potential medical emergency. The computer system 130 transmits to the dispatcher a message comprising a reason for the call, a brief personal and health information (e.g. voice automated message, or other means for which the local 911 is able to receive emergency requests). The computer system communicates the message to the 911 dispatcher, who in turn relays the message to the police or paramedics being dispatched.

Any additional requests and information that the user wants emergency responders to be made aware of are in the user's file stored on the system database, such as the need for someone to care for the user's pets and/or dependents (e.g. infants, children, elderly and disabled dependents etc.), relatives and friends to contact, allergies, special message to the rescuers to notify emergency professionals of a particular need the user may have, of appropriate treatments, and stop them from attempting potentially harmful treatments etc. This information is contained in the brief report the computer system 130 gives to the 911 dispatcher via the automated call. This information is then relayed to the paramedics on the scene who are responsible for ensuring that pets and dependents are cared for if the user is taken to a hospital. Additionally, or alternatively, the computer system 130, or a call center with live human attendants associated with the system 130, may contact the user's listed contacts by order of preference to arrange for them to go to the user's residence and take care of the user's pets, dependents, secure their property, etc.

The user can also request that special messages/info regarding their children/minors at home, disabled adults and animals under the user's care be supplied not only to the emergency responders, rescuers, police officers, and designated caretaker(s), family members or friends, but also to health professionals and/or clinical social workers etc. along with user's advance directives for those children, disabled adults or elderly and animals, any diet restrictions and food preference for example, as well as rent or mortgage information including their contact company/person(s). The user can also supply bank information and other financial documents to be passed on unofficial/temporary/long-term guardian for the care of the user's children during user's hospitalization or after user's demise, etc. Users can supply any information they want to supply.

In step 630, the system 130 then determines if the user's record has a "medical authorization code" to protect the user's medical records stored on the system database, comprising information such as if the user has any special medical conditions that medical professionals treating the user need to be aware of (e.g. allergies to medication, pre-existing medical conditions, medication currently on, physicians who are treating user, etc.). If yes, then the system 130 transmits the code to the dispatcher (e.g. voice automated) (step 640); and, if not, then the system ends the 911 call (step 650).

In step 640, the computer system 130 further tells the dispatcher that the code is to access the medical records and asks the dispatcher to give this code to the police and paramedics responding to the rescue, who will use it to access the user's file or who will provide it to hospital staff upon arrival at the emergency room. Additionally, or alternatively, all dispatchers will know that the code is to access the patient's medical record and they will also know what to do with the code because of prior communications (e.g. notices, advertisement, training, in-service etc.) given to 911 responders, police officers, hospital staff, and paramedics.

Additional user information, such as advance directives, insurance information, next of kin etc. is also shown along with the medical record once the code is activated.

In step 660, the computer system 130 receives an electronic transmission from the hospital emergency room (E.R.) computer 116 comprising the user's medical authentication code. In response, the computer system 130 electronically transmits via the network 120 the user's medical information stored in the user's record protected by the code to the E.R. computer 116.

In an additional embodiment, if the user is conscious/alert, then s/he can also issue a permanent or temporary access code/authorization code from the mobile app 160 on their electronic computing device 110 (e.g. smartphone) and give this code to emergency professionals, to the ER, to treating physicians, to other health entities or health professionals or whoever the user wants to allow access to their medical records, who in turn will access the user's medical records via their own computer system if it has the present invention/system integrated or via the present invention/system's web app. But, a non-user would need direct access to user's device 110 to view any information unless the user chooses to give them direct access.

The computer system of the present disclosure may also be integrated within the hospital's computer system allowing the hospital to access and even issue a code to user themselves that will be recognized by the computer system (e.g. server 130). For example, they may issue a code in cases where a patient/user is setting up her medical folder for the first time. For example, each hospital may have an application program interface integrated into their computer system that allows the hospital's system to access the user's medical records stored on server 130 from the emergency room computer 116.

That information can be obtained directly from the communication center (computer system 130) or from their electronic computing device 110 using an authorization code, a username and password given to them by their employer which in this case is the hospital, but there is no syncing happening. However, retrieving the code via the hospital system 116 also allows automatically syncing/backup of the new health findings/data from the ER into the computer system 130 and 116. The doctors' office will also have that same API on their computer system to be able to sync current health data so that computer system 130 will always have up-to-date user-patient information, such as the diagnosis and treatment given to the user in their visit to the ER. By allowing health professionals to have up-to-date medical records, the system significantly increases the accuracy of diagnoses and treatment and decrease medical errors. Additionally, unsecure transmission of health information by fax, email or SMS can create enormous risk if fallen into the wrong hands. To solve this problem, this invention puts the security control, privacy and confidentiality of user's electronic health records into the user's hands. With the system's rigid privacy, users not only have the power of control over all their data, but they also have ownership over all their data. The system's administrators do not have access to users' data unless users specifically give them the permission to access their data for the purpose of providing users with better support. With this system, not only transmissions can be blocked, but also all transmissions are encrypted, tracked and leave an audit trail. Users can make the system do what they want it to do. Everyone has the right to require that their health information be kept confidential and have control on who accesses their health information. This system gives users full control on who sees or accesses their health records as well as set a time limit on the access given i.e. how long and what they can do with it. With this system, users can give screening access only, restrict printing and downloading, making their record disappear when the clock reaches the specified period of time set, requiring rigid login using a set of access code, password, signatures, pin numbers, iris or facial recognition and any other appropriate mean of recognition, fingerprints (via the integrated fingerprint sensors) etc. For example a user can give a health professional access for two hours only.

Only health entities have the ability to "add" information to the user's medical records. The user can also read/access/print/download their own medical records (objective data from health professionals) but they cannot add, erase or alter their medical records. They can only add their subjective data (self-evaluation/report) files into their subjective data folder which is also within the medical folder.

Legal Records

Figure 7:
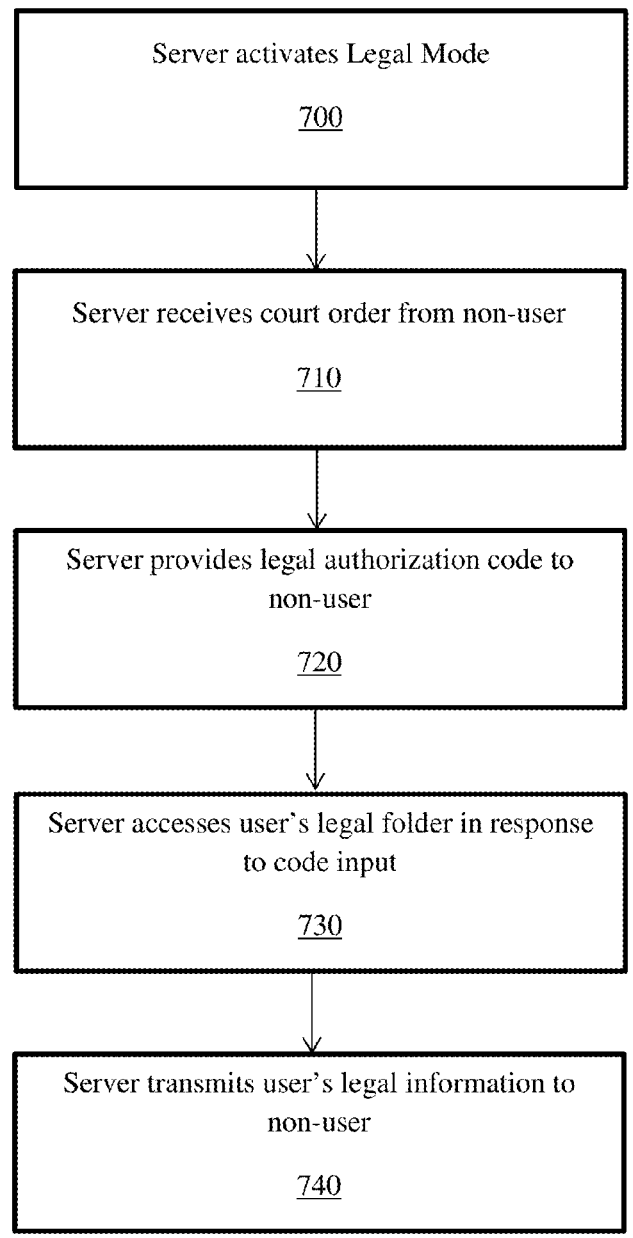
FIG. 7 is a flowchart of computer steps allowing a non-user to access the user's stored legal documents.

FIG. 7 is a flowchart of steps in the event that the user dies or is incapacitated to the point of not being able to make their own decisions regarding their medical care. The user's legal information, such as their last will and testament, living will, life insurance policy, trust funds, assets information, etc. are stored within the legal folder of the user's file on the system database. This legal folder requires a separate code, the "legal authorization code", for someone other than the user to access it, and this code is different and separate from the "medical authorization code". After, a user's demise, the legal authorization code is available by court order and with that court order, the specified information can be obtained directly from the system server 130, or via the system's advanced communication center or its affiliates.

In one embodiment, step 700 comprises the computer system activating the Legal Mode (module). In step 710, the computer system receives a copy of the court order from a non-user who has been given authorization, such as an executor of the user's estate. In step 720, the computer system provides the "legal authorization code" to access the document(s) specified in the court order to the non-user when the authenticity of the court order is verified. In step 730, the computer system accesses the user's legal folder in response to code being input into the system. In step 740, the computer system transmits the specified user's legal information to the non-user.

Monitoring Vital Signs Remotely

The various embodiments of the present disclosure are also able to monitor the user's health remotely to detect if the user is having medical problems. Health parameters measured comprise, for example, clinical vital signs, heart rate, blood pressure, blood sugar, EKGs, oxygen saturation info and other lab values etc.

Figure 39:
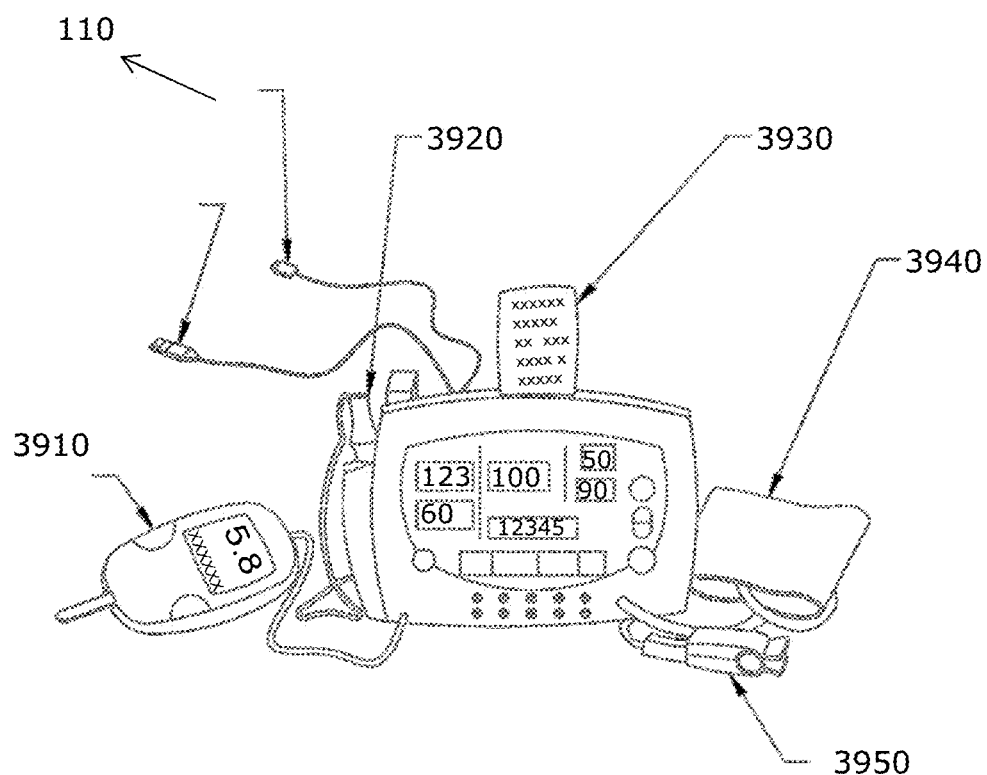
FIGS. 39 and 40 illustrate two versions of a medical device(s) to detect vital signs.
Figure 40:
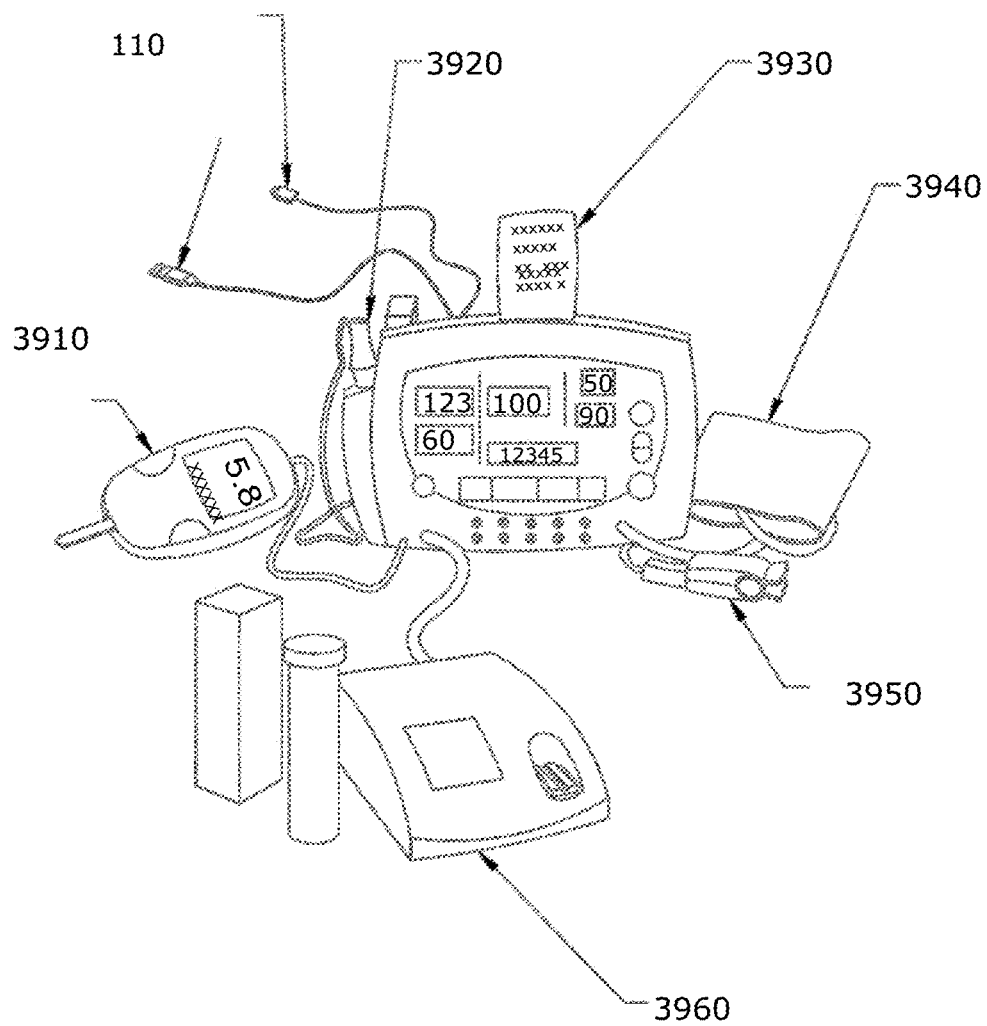
Figure 41:
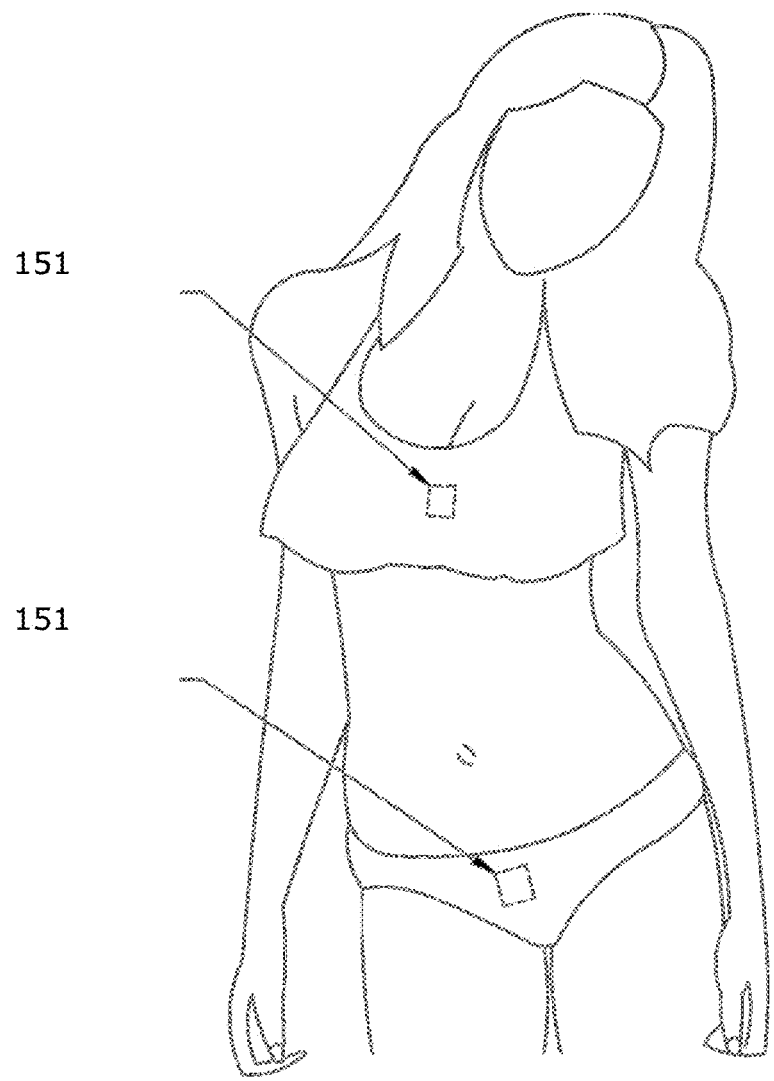
FIGS. 41-51 illustrate various items of clothing and accessories with GPS chips inserted therein for use with the present invention.
Figure 42:
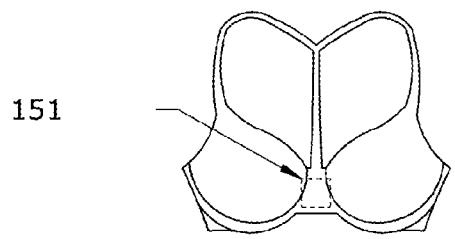
Figure 43:
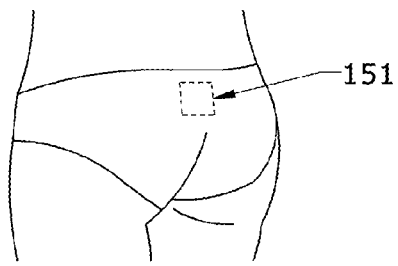
Figure 44:
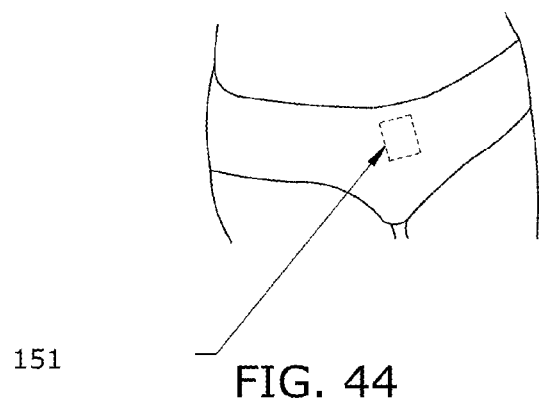
Figure 45:
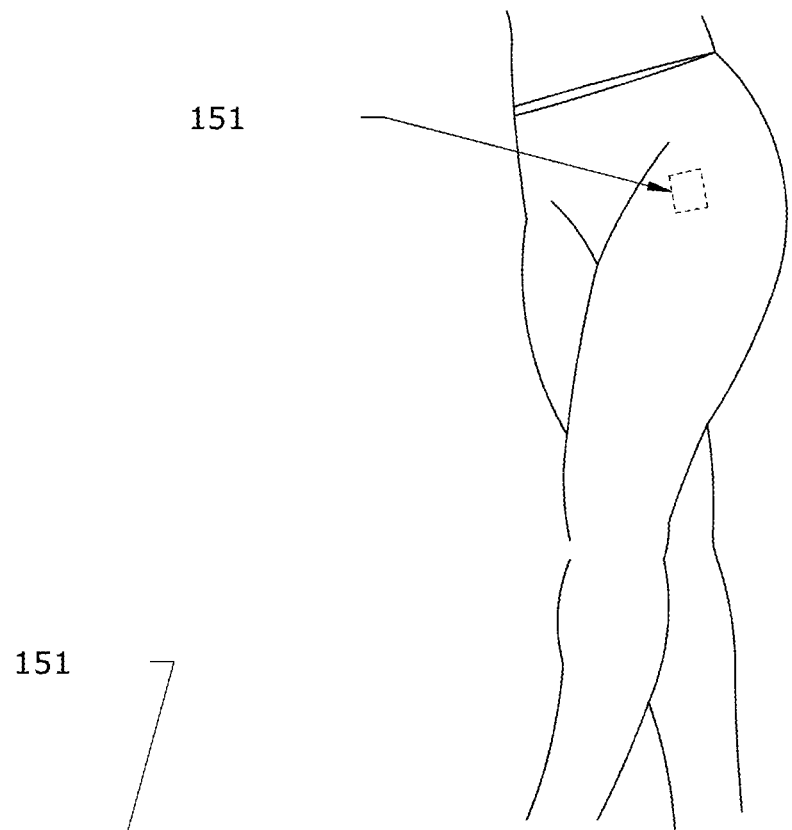
Figure 46:
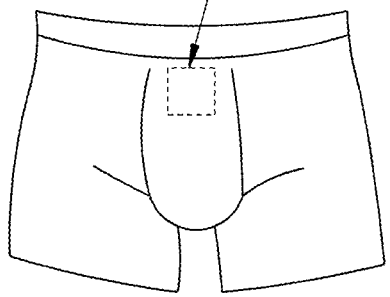
Figure 47:
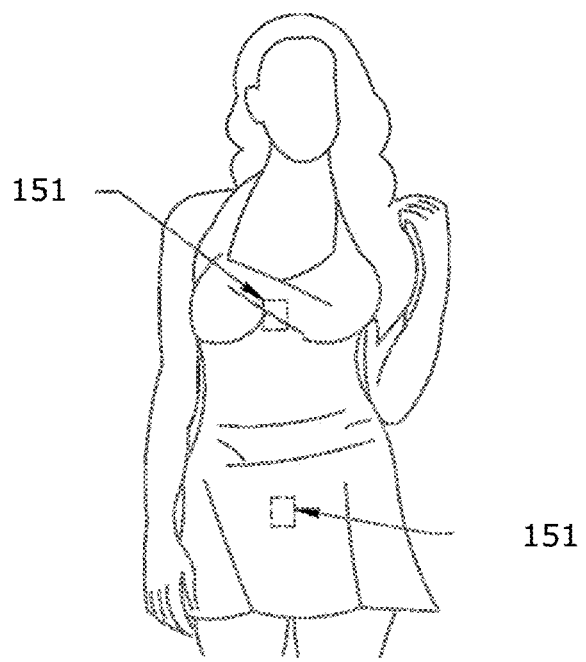
Figure 48:
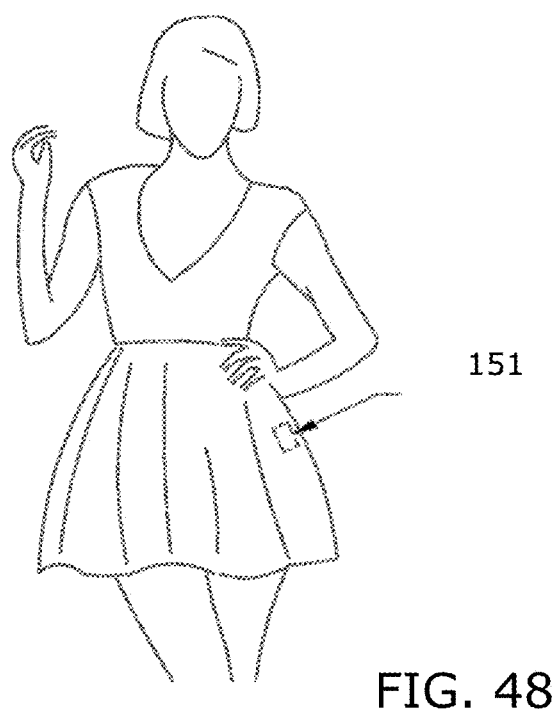
Figure 49:
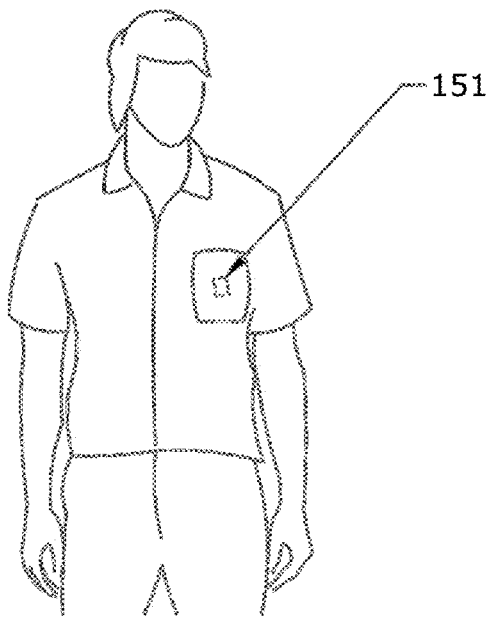
Figure 50:
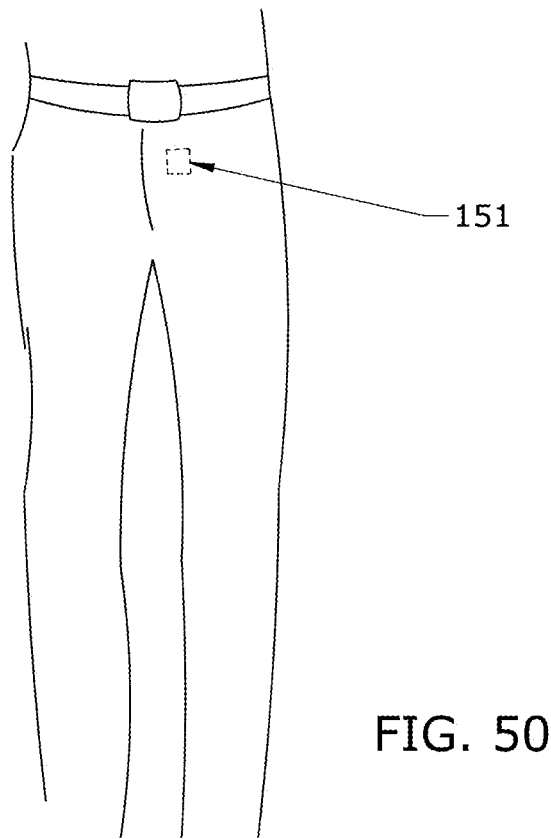

In some cases critical values may be obtained via: (i) the device; and/or (ii) the-app's own integrated or non-integrated tools or features; (iii) and/or via connected/not connected and/or integrated/nonintegrated, wireless and non-wireless proprietary or third party tools that take and/or monitor (in real life) vital signs that include, by way of non-limiting examples: blood pressure, heart rate, temperature, heart rhythm—blood sugar level, oxygen level, blood medication levels, alcohol level, other blood chemical levels etc. and/or (iv) in absence of movement from user and/or absence of breathing, loss of consciousness etc. Other self-initiated monitoring in non-critical cases are habits-based and may be done via a series of random calls throughout the day or using alternate or more appropriate methods. FIG. 39 illustrates an exemplary device for monitoring vital signs comprising: a blood sugar device 3910; measure temperature 3920; EKG 3930; blood pressure monitor 3940; pulse oximeter 3950; USB connector, and connector to smartphone 110. FIG. 40 illustrates another exemplary device for monitoring vital signs comprising: a blood sugar device 3910; measure temperature 3920; EKG 3930; blood pressure monitor 3940; pulse oximeter 3950; USB connector and connector to smartphone 110; and urinalysis device 3960.

Figure 35:
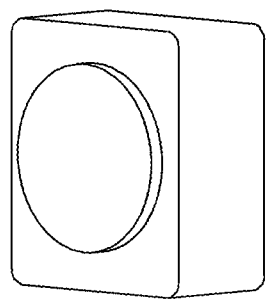
FIG. 35 is an illustration of an emergency button with an adhesive back.
Figure 36:
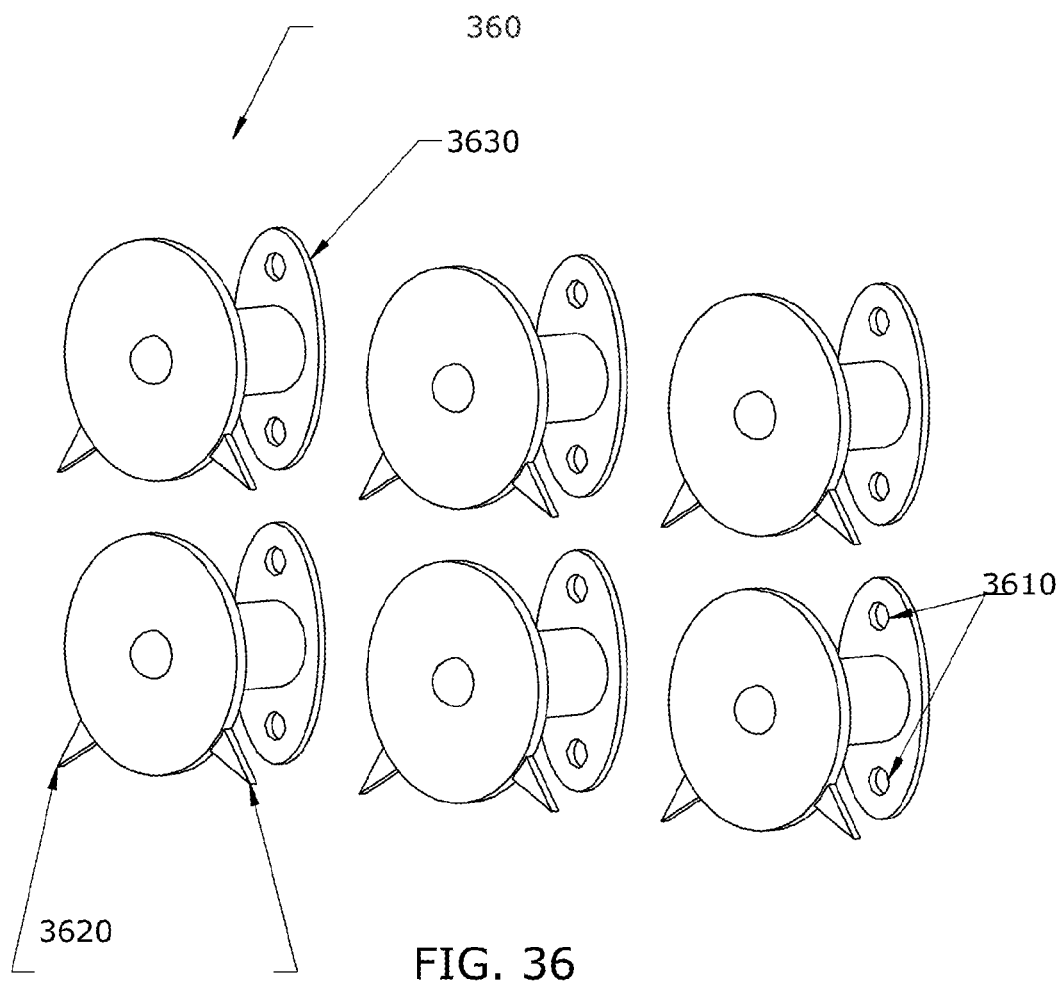
FIG. 36 is an illustration of various wall mounted speakers.

Another solution for when users forget to turn on their phone and the app, is the removable and wireless stick-anywhere emergency buttons with speakers strategically placed throughout the home and which when pushed, connect the user to the support center for support and/or activates the monitoring mode depending on user's preset orders. (See FIGS. 35 and 36 for non-limiting exemplary embodiments). The emergency buttons with speakers 360 as illustrated in FIG. 36 comprise one or more of: holes 3610 to hang; legs 3620; and adhesive backs 3630.

Safety Features: Critical Values Monitoring—Disease Diagnosis & Treatment—Disease Prevention & Follow-Up—Disease Management.

Real-Time Monitoring of Critical Values. There are actually three methods in which basic vital signs values in general can be obtained, as well known in the art. 1) In a first method, by uploading the data in real-time from third party medical diagnostic equipment hooked up to the user's electronic computing device 110 (e.g. blood pressure machine synched to smartphone). 2) In a second method, by obtaining this data from the electronic computing device itself with or without the use of third party medical diagnostic equipment which will then share the data with the computer program product of the present invention. 3) In a third method, via the app's own vital signs medical diagnostic device, such as an all-in-one equipment that reads the data so that the user does not have to use many different diagnostic devices to obtain different readings. See FIGS. 39 and 40 for exemplary devices.

In all three methods, system 130 or device 110 with the app 160 reads the data obtained from the third party tool, and analyses the info for critical values, trends, baseline values, reference values etc. If a critical value is found (i.e., potentially life threatening), the system 130 or app 160 makes a decision based on current protocols, such as inform the user on what to do to do resolve the issue, and/or initiate an automatic call to 911 depending on the severity of the increase or decrease compared to the normal values. In other words, the system recommends steps to take to mediate the problem while waiting for paramedics to arrive, if official emergency help was required. If a value is life-threatening or the patient is incapacitated, the system will notify 911 (for USA) immediately and also the user's loved ones if allowed.

Competency and the capacity to make decisions: The system is also able to assess if a user is not competent to make his/her own decision through a poll when a user forbids the system from calling 911 for a confirmed emergency situation, such as when a critical value is depicted. If the system determines that the user is incompetent, the user's order may be bypassed and an authorized party such as a person pre-selected by the user to act for the user in cases of incompetence/a person having power of attorney will be contacted. This event may also prompt a dialogue with the Support Center who may choose to intervene to make sure the user is safe. If the issue is pressing, or a pre-selected user with power of attorney was not selected, or a next of kin cannot be located immediately, the system will carry on with emergency alert to emergency dispatcher who will then API decide how to proceed.

Prevention—Diagnosis & Treatment Suggestion. Whenever the vital signs and labs values deviate considerably from the user's baseline, or whenever the system finds that the user is at risk for a certain disease, it will alert the user to these changes in medical condition, provides a diagnosis and suggestion of treatment to discuss with a doctor in order for user to get timely medical treatment. This feature is referred to herein as a "personal digital doctor." It works pretty much the same way an actual doctor performs a consultation or issue a diagnosis. How does this preventive feature work? Once the computer system obtains the labs and vitals values, the system will analyze these values for abnormal versus abnormal, critical vs. non critical, high vs. low, increase vs. decrease from previous values, trends, current protocols, scientific studies, reference ranges, the user's baseline, the computer system will compare any picture or video of signs or manifestations of a disease against existing database for a match etc. If the computer system finds that a certain value or variable could represent a risk to the user's health, or potentially be a sign of an upcoming illness, or could possibly lead to a potentially life-threatening condition, the system will automatically pair up this information with key elements from the patient's past and current health information and medical records, and analyze this information thoroughly, both against current and past trends and studies and against family history to issue a diagnosis and suggest treatment to discuss with a doctor in order for the user to obtain timely medical care. Preferably, the user has a primary care physician on file. This information will be forwarded to their primary care and other doctors as indicated by the user. The diagnosis result and treatment suggestion (whether medical or psychiatric) will randomly popup to user's screen on a daily or weekly basis via push notifications, SMS or other applicable means until the user confirms that the issue was taken care of. If the person had non-desired/abnormal blood pressure that did not warrant an emergency response, the system activates the random call on a shorter period of time than normal for example every two hours throughout the day or as desired by user until new blood pressure values are taken/registered and confirmed as being within normal limits.

In addition to a drug reference, the system will incorporate a database of known diseases, their signs and symptoms and treatments and evidence-based practice. Changes in conditions will be recorded not only by detections of abnormal and critical vital signs but will also be search, keywords and vitals driven and these mechanisms will be reinforced by random polling and automatic detection based on user's queries within the app's health resource catalogue/reference, users' complaints, messages, and answers to random questionnaires asking: "is everything OK?" "what's wrong?" or "how are you feeling today?" Other random interrogations may be presented, also based on search queries made by user in the disease management hub, interests voiced by user, conversations or conference, keyword between user and emergency contacts or loved ones, missed/non successful/inconclusive monitoring requests (i.e., monitoring requests that don't end up in a completed emergency mode/alert). For example, if a patient has a blood pressure that is a slightly outside the normal range, the user may be checked that s/he is not feeling well as a reason for a monitoring request. Following the same path and tactic a real doctor would use, the user will receive a prompt for an interrogation/survey (i.e., this user might be invited to answer a series of key questions about current activities, health state, lifestyle, and how they have been feeling lately. If these results are repetitive, the app will conclude that something may be wrong, and will seek further information to streamline and fine tune the right diagnosis and treatment (using evidence-based practice) and advise/suggest accordingly that patient talk to their doctors about findings. Each successive prompt will be a step closer to a diagnosis. Meanwhile, the back end of the system is determining and fine-tuning through a collection of many possible diseases/health issues. No more absent queries through the Internet to surf and read about what could be wrong with the user. Using evidence-based practice, the system will provide users with focused diagnosis. Users can also press on the button "Diagnose Me" at any time or whenever the user is not feeling well which follows the same process. Users can also be randomly polled to answer health and state of well-being questions and answers to these questions will be processed in the same fashion as answers through direct inquiries. The system will determine how often to poll a user depending on availability or non-availability of health information (i.e., health status, health condition and/or medical information on file). In the case the user's condition/disease is suspected as being epidemic, further action might be needed to prevent its spread according to current laws in place.

Medical professionals can also use the system drug reference and the app disease management system to prescribe medications to their patients. The computer system allows and facilitates input of medication orders within the user file, computer server verifies order for accuracy against user's medical records for allergies, relevance and against evidence-based practice and integrated or non-integrated drug references. The computer system gives results: including ready for signature, suggests an alternate drug that is more appropriate for the user, and requests that order be revised. Once order is signed, it is made available to user who will receive a notification that a new order is on file. The user will in turn decide what to do with any new order. If the user desires, s/he can choose to have the order filled electronically and even delivered.

Diet Safety. As part of its preventive health safety, the computer system not only alerts users if they are at risk for certain health problems, or changes in conditions, the system also watches the user's diet, suggests a diet to user based on user's current health status and warns user against non-recommended or potentially harmful diet to the user's health. For example, the system will warn the user if the food he/she is about to eat will exacerbate existing medical conditions. How is this done? The user inputs in the food he/she plans to eat or is about to eat and the system analyzes the information generated or inputted in about the food against the user's current health status utilizing all health info it has regarding the user, recent and current scientific research and studies, evidence-based practice and current protocols to determine if the food is safe for the user. In the same fashion, when a user goes shopping for food, the user can scan a desired food product/item using the system's scanner, and the system can tell the user on the spot whether or not this food is recommended or is beneficial to the user's health.

EXEMPLIFICATION

Remote Monitoring (Parent/Child)

For added convenience, anyone can register/set up the app physically/in person or remotely, which means users can program the app for their loved ones or they can program the app on their own computer or devices to monitor their loved ones. How this is accomplished? For example, Megan wants to monitor her elderly mother, Mary, who has a history of or suffers from seizures. Mary is an elderly lady who does not like electronics; she absolutely does not want to deal with a computer or a mobile device. The only thing she is comfortable doing is answering the phone. Megan had downloaded the app on her own computer and mobile device and registered her mother. Since her mother just announced to her that she is not feeling well because she believes she has an aura, and Megan is in a meeting at work, Megan confidently programs her own activated app to monitor her mother, Mary, according to her own criteria. For example, Mary may ask the app to call/text/alert her mother's regular telephone or mobile phone, or tablet or computer. The apparatus does not need to have the app installed to receive calls from Megan every three minutes for a period of an hour, for example. If her mother does not answer, then the app calls/texts/alerts Megan. If Megan cannot answer, the app calls 911 and passes along Mary's medical information to the paramedics; all this without anyone having to touch or do anything. In this way, Megan can continue her meeting with the peace of mind of knowing that her mother is being effectively monitored and she will receive emergency care if she needs it. This also means that older people will be able to easily use the app and/or the services offered by the app. Users do not have to be computer literate at all and they do not even have to touch the app or learn how it works in most cases, although there is very little learning involved because it is ultra-intuitive. Illiterate, deaf, blind, people who have vocal problems or other disabilities and even people who do not have the use of their hands can benefit from it. In cases of remote monitoring by a loved one, the end-user may use any regular telephone/cell phone/VoIP, etc. What this means is that the user-beneficiary being remotely monitored may answer/not answer depending on the circumstances. However, he/she may not be able to modify the monitoring settings if the primary user who is doing the remote monitoring locked the settings and/or that option is unavailable in cases where the user-beneficiary has a phone with no interface or no additional gadgets with the required features.
Safety Feature—Victim of Crime For confidentiality and security purposes, in addition to being able to make the app disappear from the screen using a combination of keys from within or outside the app, there is a button at the bottom of the app that allows users to easily hide the app. Users are able to change the app's icon to another desired icon or other alternatives to icons if user wishes to mask having this life-saving app on their phones. This in cases of terrorism and other cases where the user's life may be in danger just for being in possession of this app.

A very important feature of the app is that it can monitor many individuals at once and alert families of children wandering away or kidnapped. The app connects all the users in a family together, a family can use it for many users at once, and all the users have real-time automatic location of each other. The main user determines this so that it cannot be blocked or altered by a child. The system also records what's happening in the environment. It is understood that a kidnapper can always outsmart the system by striping the child naked, and by trashing the phone and any safety accessory the child is wearing. However, the ability to put the system into the Monitoring/pre-emergency/emergency mode is what is priceless because if the child had some suspicions, he/she can put the system on silent monitoring beforehand for help to arrive immediately. The ability of the app to randomly monitor is also useful in cases of kidnapping where the child did not have the time to request direct monitoring. To counter the possibility that the kidnapper may dump the child's phone in the trash before taking off, a parent may pair the app with a miniature GPS-location based hardware which can be hidden anywhere in clothing or hair, glued to the skin, to shoes, to socks and even be worn as a normal hair accessory. The miniature GPS is so tiny that by the time the kidnapper finds it, emergency help might have already detected the child's location. See FIGS. 15-30 and 41-51 for exemplary embodiments of hidden miniature GPS chips in two embodiments 151, 161.

Figure 15:
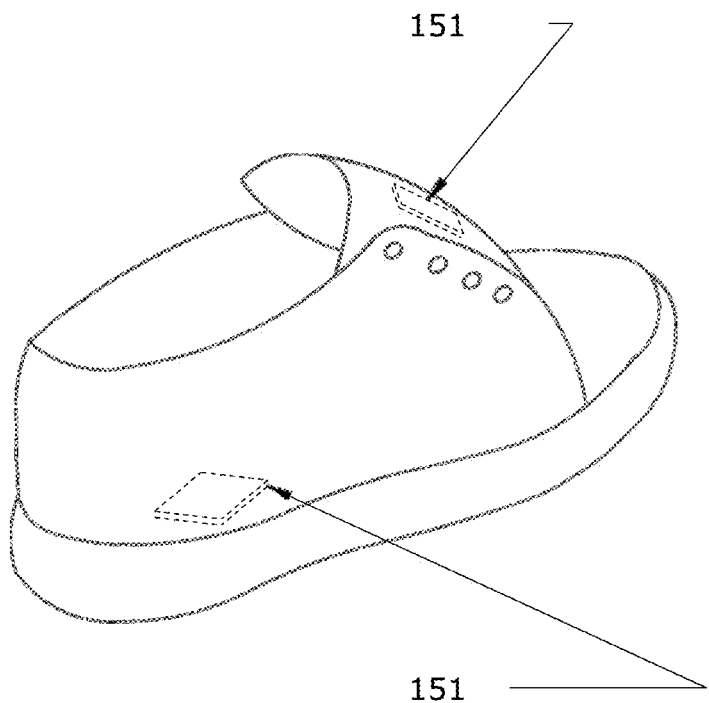
FIGS. 15-30 illustrate various items with GPS chips inserted therein for use with the present invention.
Figure 16:
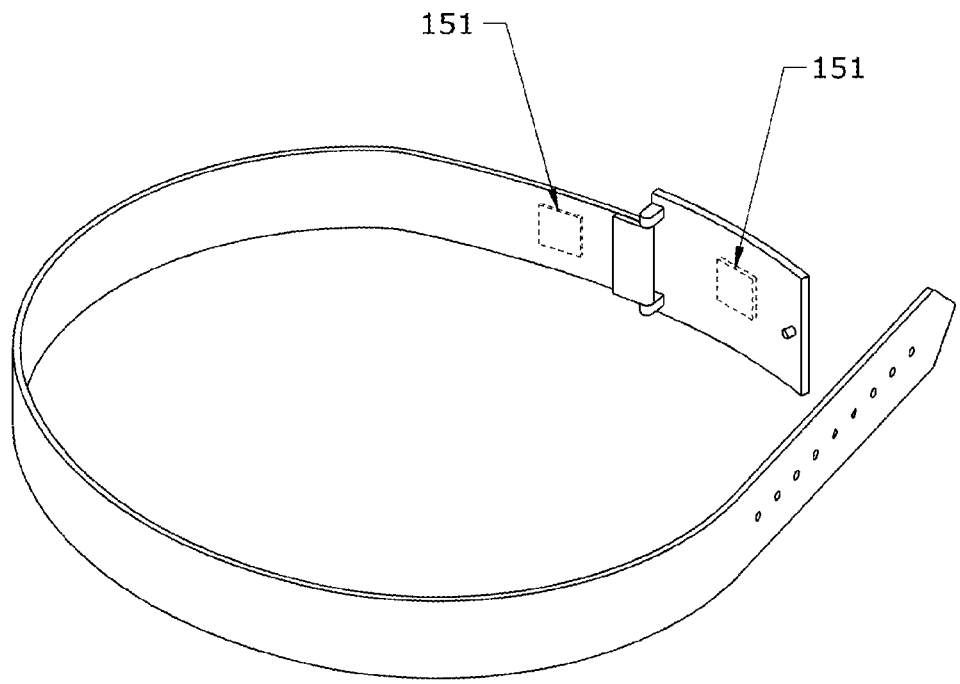
Figure 17:
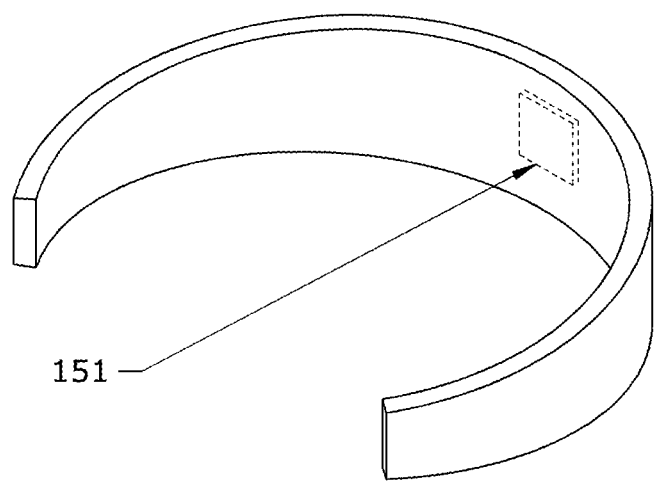
Figure 18:
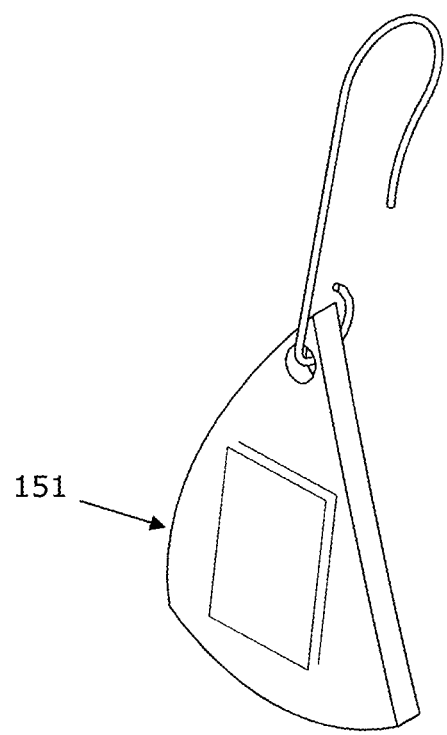
Figure 19:
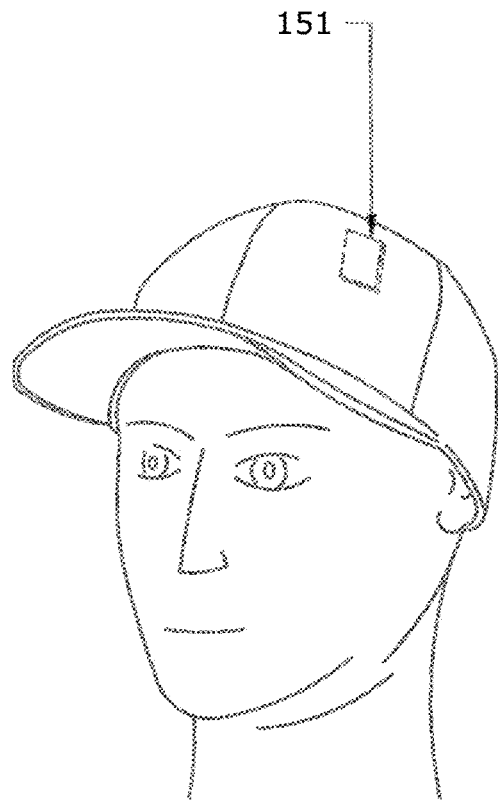
Figure 20:
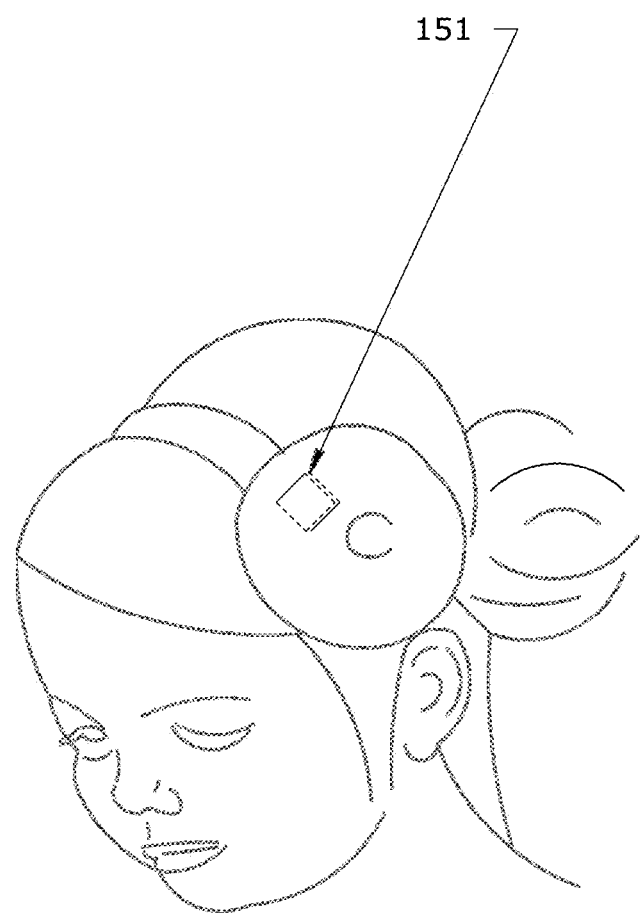
Figure 21:
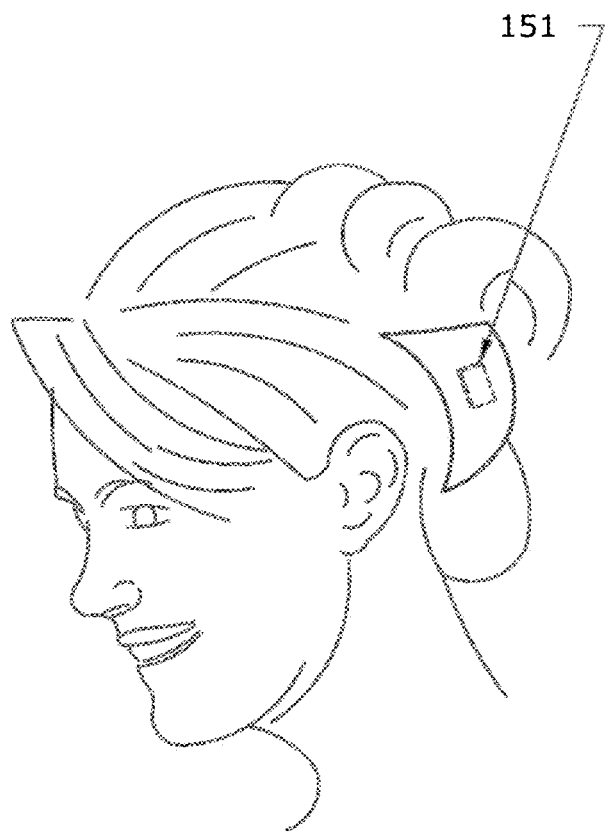
Figure 22:
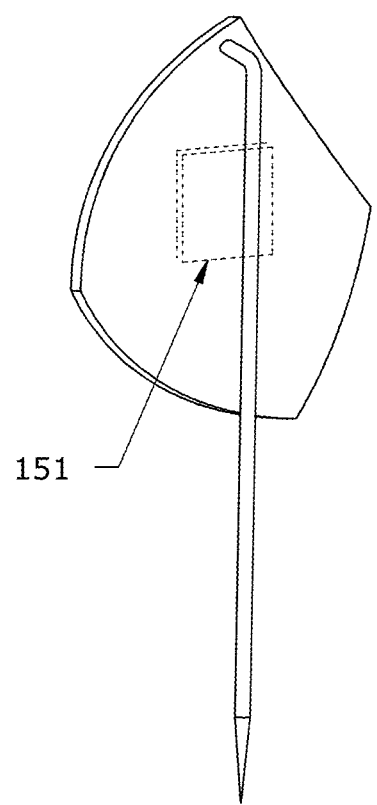
Figure 23:
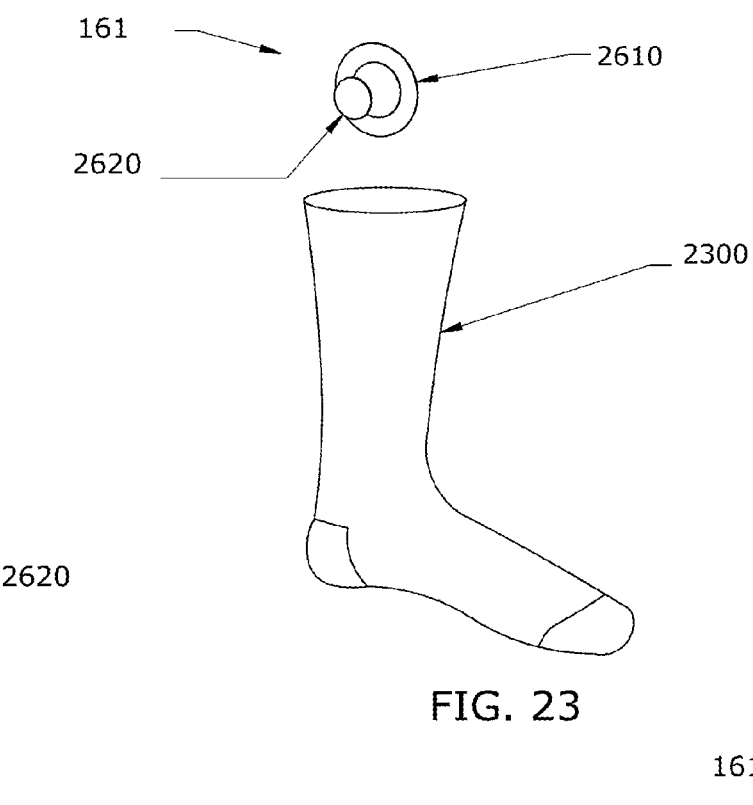
Figure 24:
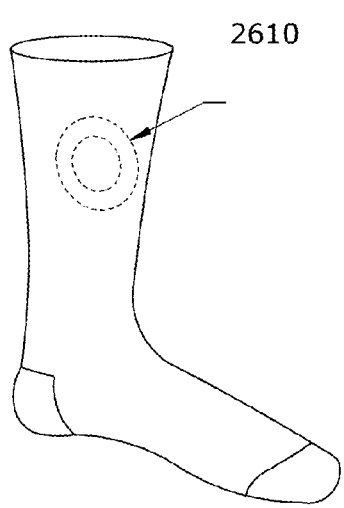
Figure 25:
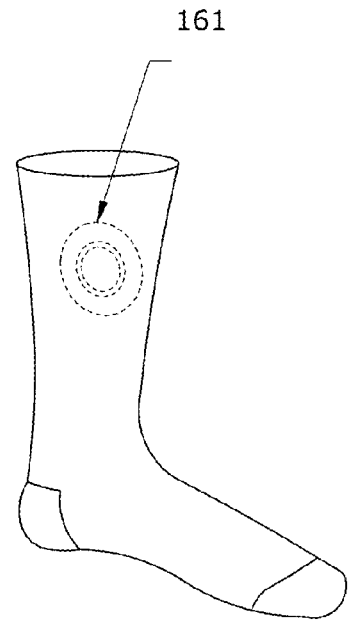
Figure 26:
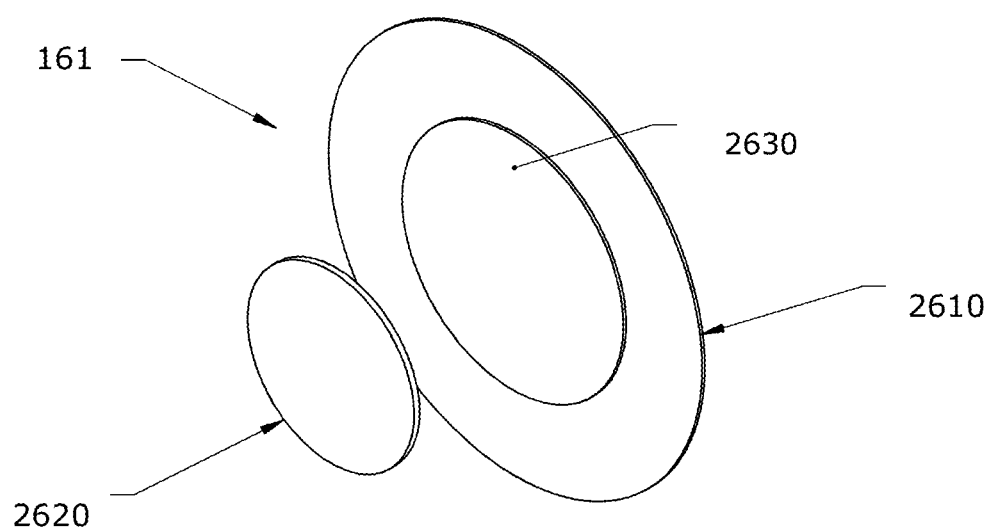
Figure 27:
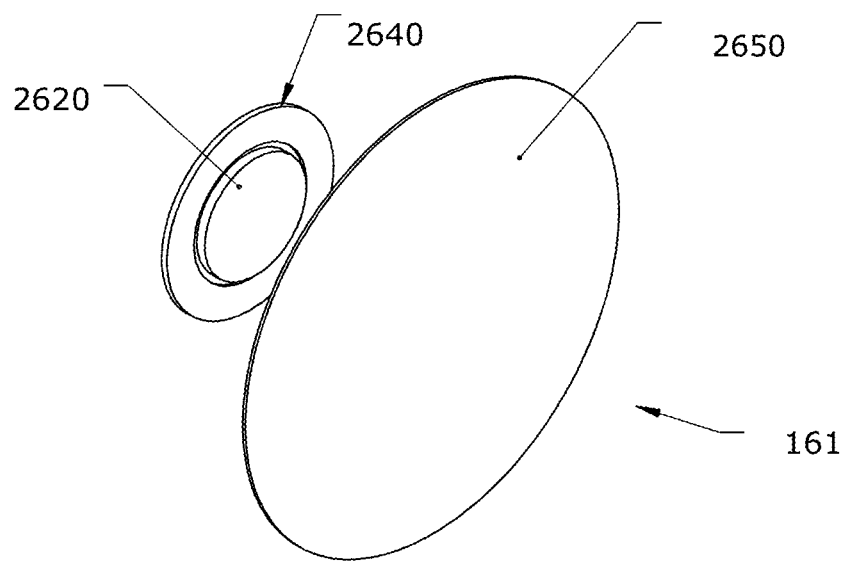
Figure 28:
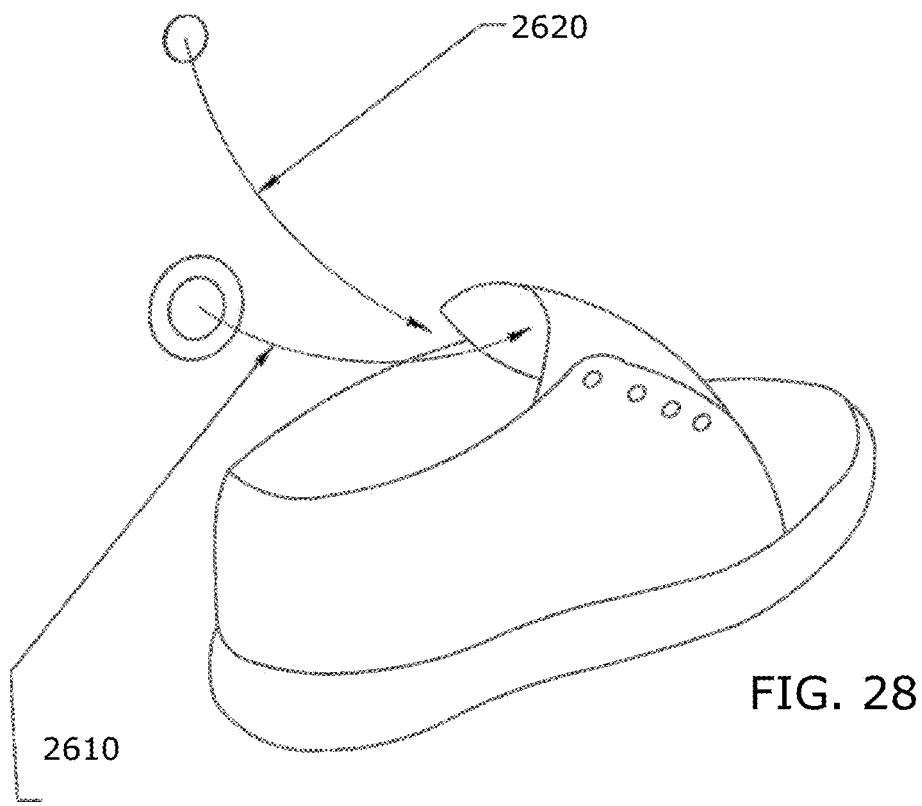
Figure 29:
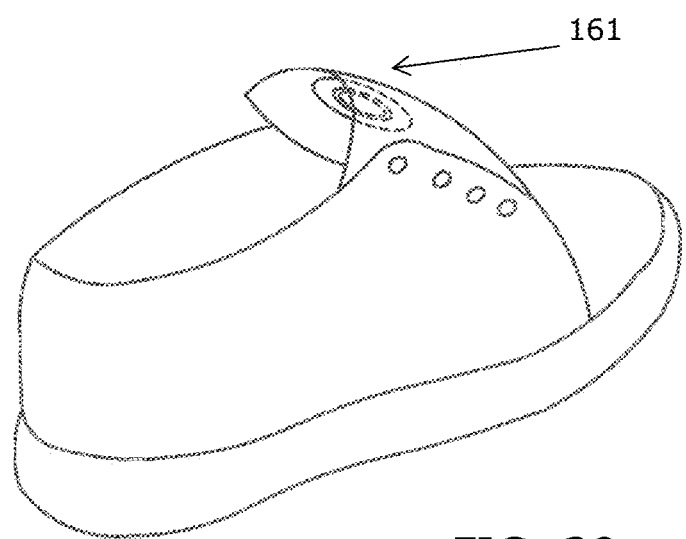
Figure 30:
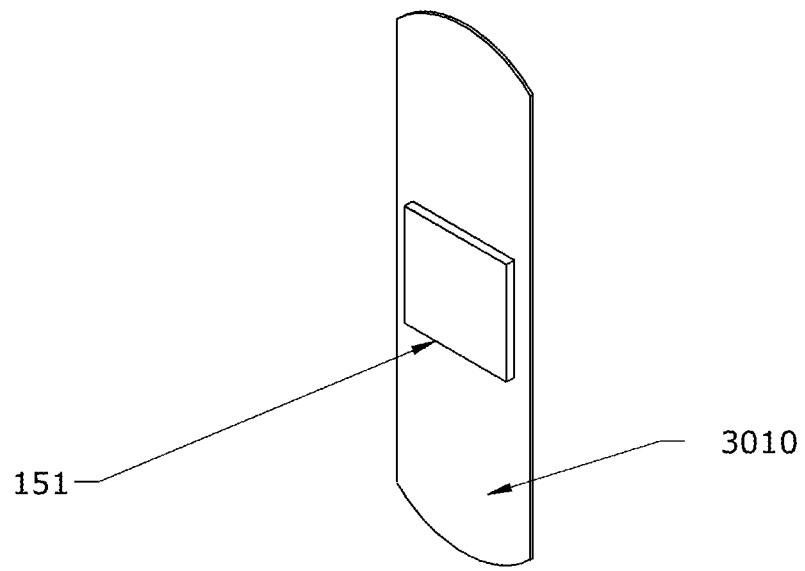

FIGS. 15-22, 30, and 41-51 illustrate a first embodiment. FIG. 15 illustrates the miniature GPS 151 in the shoe sole and/or the shoe tongue. FIG. 16 illustrates the miniature GPS 151 in the belt buckle and/or belt leather. FIG. 17 illustrates the miniature GPS 151 in a hair headband. FIG. 18 illustrates the miniature GPS 151 in an earring. FIG. 19 illustrates the miniature GPS 151 in a hat. FIG. 20 illustrates the miniature GPS 151 in a flower of a headband. FIG. 21 illustrates the miniature GPS 151 in another headband. FIG. 22 illustrates the miniature GPS 151 in a brooch. And, FIG. 30 illustrates the miniature GPS 151 attached to the adhesive layer of a band-aide 3010.

Figure 51:
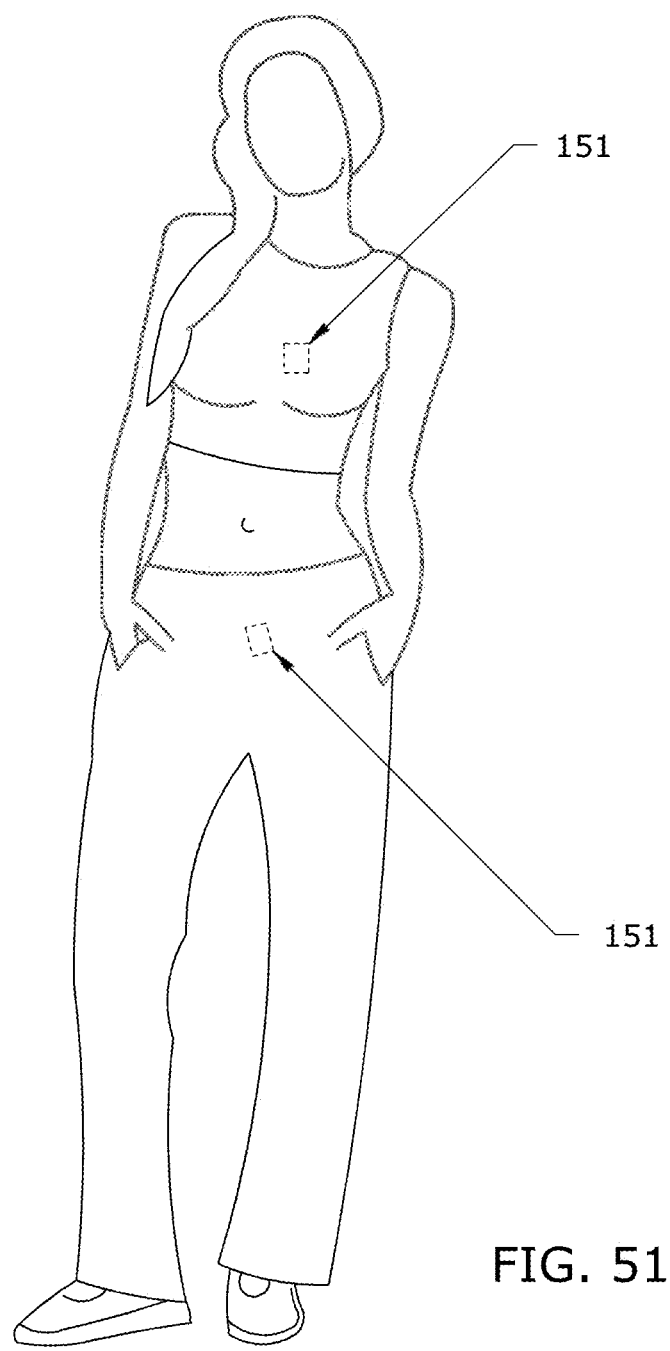

FIGS. 41-51 illustrate the miniature GPS 151 hidden within men's and women's clothes: bikini bathing suit (FIG. 41); bra (FIG. 42); back of panties (FIG. 43); front of panties (FIG. 44); women's hose (FIG. 45); men's briefs (FIG. 46); women's dress (FIG. 47); women's skirt (FIG. 48); men's shirt pocket (FIG. 49); men's pants (FIG. 50); and, women's T-shirt and pants (FIG. 51).

FIGS. 23-29 illustrate a second embodiment of a hidden miniature GPS chip 161 comprising two parts: outer loop 2610 and inner disc 2620. The outer loop 2610 comprises an inner ring 2630 in which the inner disc 2620 snaps into 2610 using hooks 2640. The back of the outer loop 2610 comprises an adhesive layer 2650 the enables the GPS chip 161 to stick to material, such as a sock.

The app has many other potential uses. For example, a user can put the system into monitoring mode if the user is planning to meet a stranger (such as a blind date), or if the user is in the process of answering the door to a stranger, or if the user is going to a dangerous area or is vulnerable at night. In such situations, the user can program the app on "Monitoring mode" as explained above and the app is able to provide not only location information to your rescuer but also all other crucial explanations possibly needed for an optimum rescue. The app can also save its automated communication exchange with emergency response personal, if this option was selected. Users are encouraged to have the system monitor them even if they don't think a malaise is serious. They can input whatever time length they prefer. For lengthy time length, the system can randomly call repetitively throughout the day.

Medical Records Code

Code generated by the system. When the app calls 911 or the country's emergency number, it also generates a code. As a reminder, the user and the communication support center can also generate this same code. It is an access code to retrieve the user's medical records/information. The health professional(s) caring for the user or the person(s) chosen by the user to have this code can either check/retrieve the private information online themselves via the web app or via the system API installed on their computer system or via a live person at the app communication/support center, or by any other means legal and compatible. Of note, the user has a choice of requiring from the person or entity processing the access code to retrieve the user's private information a combination of fingerprint, iris or facial recognition plus verifiable pieces of information, and/or real-word identity verification online, and/or offline to access confidential information, such as authentication via answers to questions generated from a public information database. In this type of verification, users can require that the person or entity confirm personal historical data about themselves to make sure they are who they claim to be.

As described above, when the system calls 911 as predictated/pre-requested by the user, in addition to providing the 911 dispatcher with all the information relevant to the situation, including user's identity, circumstances preceding the emergency situations, the user's current location, needs and care coordination for children, other dependents and pets that are under the user's care, special message requesting not to attempt a potentially harmful treatment etc., a code is communicated to the 911 receptionist. This code contains the user's information, their identity (including pictures), health info, the user's advance directives, identity, etc. The 911 receptionist in turn passes that code on to the paramedics and/or police officers who are called to the scene or responding to the emergency. This way before they get to the user's location, the responders can check the user's health info before they even get to the scene, or on their way to the scene.

How is the health information obtained/retrieved? The entity/person with the code calls/texts/alerts the communication support center for the information, or logs onto the system with the required credentials (e.g., name of requester/name of company/username/passwords), and retrieves the information needed with the code. A support person or the system will provide all the information needed to provide an ultimate rescue, such as:

identity
pictures
health info, medical records
demographics
current conditions
signs and symptoms
baseline vital signs
most recent vital signs
past/present EKG results
oxygen level
recent/current labs values
current allergies
current medications
specialists following
specialists' assessments/treatments/recommendations/plans
specialists' contact info
past surgeries
past medical history
family medical history
next of kin
emergency contact
insurance(s) info
health advance directives
aggravating and alleviating factors
subjective data including possible causes according to user's point of view
past medical history
any contraindication for a specific treatment
past and recent hospitalizations
severity of illness
durable medical equipment at home
other medical equipment
home assessment
psychosocial info
disability status etc.

In addition to the automatic update that is done via the system API installed on the hospital's computer system every time a patient medical record is accessed, if a hospital does not have the system API installed, the system allows users to request, upon discharge, that their medical chart be uploaded to the system via the web app or directly into their smartphone by the hospital treatment team. Any of these options automatically updates the medical record on file in the system. This way, users can have their up-to-date health information in their possession which would be extremely valuable during follow-up medical visits in order to prevent duplicate medications/treatments/regimen. The user will also be able to give future treating health professionals an up-to-date health report. The secure system online database may be used as a haven/source/storage/database of medical records by all hospitals, doctors and other health entities to work, store, add, and retrieve medical records of all of their patients. Medical professionals can have access to the user's vital metrics for trends in blood pressure, heart rate, blood sugar, and other data in order to make accurate titrations in medication dosing and give overall better treatment. They can also know specific information about the user's diet like for example what the user is eating, how much is their daily intake of carbs, their physical activities' level etc. Likewise, the system may also be used as a Software As a Service (SaaS) for multipoint high resolution and true-to-life web/audio-video conferencing between health professionals around the world to securely communicate between themselves, broadcast, talk to one person or to a group, and/or talk about issues re: a patient wherever they are in the world; or between a limited and/or unlimited number of participants as appropriate, either interactively or non-interactively. For example, a specialist who wishes to speak with another specialist about a certain note written by that specialist in a patient medical records, can do so right from the system's interface on their mobile device, tablets, computer devices or other compatible devices and equipment using Wi-Fi, 3G, 4G or any other appropriate and compatible technology. Also, doctors or groups of doctors, telemedicine agencies can join the system to serve as resources for users who do not have their own doctor(s). Likewise users can record their daily activities and diet for immediate or later viewing by their doctors. As described above, users as well as health professionals can also choose to videotape, record, upload, download, delete, put on hold, broadcast health-related videos on the system's resource-sharing video-hub using a single system (the system) to do so in the same fashion as YouTube to help interested individuals who wish to learn more about a health-related subject or issue, with the exception that YouTube does not allow the actual recording of the video or to put the video on hold and this system does.

Additional Features

Various embodiments for the present disclosure further comprise a dedicated device with long-lasting batteries and to come preloaded on other machines with regular uses such as stoves, laundry machines, microwave ovens and/or on equipment or other compatible surfaces. If appropriate, it also incorporates non-battery-consuming games for the enjoyment of the user.

Another embodiment comprises unencumbering waterproof invisible or easily-hidden-hard-to-find wearable accessories with GPS built-in such as in shoes, the human body, clothing, hair etc. See FIGS. 15-30 and 41-51 for exemplary embodiments. The smart wearable/hidden accessories can complement the efficiency of the application in cases where offenders get rid of their victims' phones in which case a report will be generated to indicate that the phone no longer works or has been destroyed. Various wearable accessories with built-in miniature GPS or a combination of GSM/GPRS+GPS tracking devices with accelerometers and other fall detection devices and sensors, inclinometers, gyroscopes and other modern radio technologies and which possibly has audio and video capability and which can be disguised into normal wearable accessories, and possibly go undetectable or hard to detect by the offender. Those accessories will come in many different forms and shapes that the user can glue to their body, attached to their hair, or as a hair, ears or clothing accessory and/or hide in/attach to their socks/shoes/clothing etc. These invisible GPS would complement the app in that they are directly connected to the app and also to the communication centers and even if a kidnapper gets rid of the victim's phone and clothes, it would provide GPS location of the victim and since it is so small, the kidnapper would have a hard time locating it, which in turn would allow enough time for location detection. With a system like this, criminals and kidnappers will think twice before they engage in criminal activities. Users will also have the option of sending in their favorite accessory to be turned it into a permanent GPS tracker.

Another embodiment comprises providing hospitals, medical centers, medical clinics etc. with a white label computer program product that allows them to not only communicate with the computer system but also to initiate/issue/generate code and submit/sync/issue health info in the form of a code, a UPC or any other means/codes/algorithms appropriate to make the information being passed on more easily and safely via the system's secure channels. The user would access and/or retrieve their information via this code. Every user can use a single code to have his/her information updated across the board so that this patient's information is uniform on her phone, at the hospital and at her doctor's office with the end purpose that any entity that accesses the information using the latest code is presented with the updated information in real time. Think of the code as the social security for health care and the update and retrieval is made in a similar fashion through the system's servers/the cloud with the difference that backup would be done automatically in a similar fashion to Gmail and with the difference that the code changes regularly and render the previous code nulled, as per user's request and the information contained is hacker-proof secure. This would negate the fact that patients have to physically go to Medical Records departments to have their health info/reports transferred/synchronized. This applies to the hospitals or any other places that have a separate Medical Records department and require patients to physically go that department to retrieve their health information securely and effectively. In this case the information could be stored on the cloud/app server instead of being on the user's phone and occupying a large memory space.

How does the app work when the phone is out-of-power? If the app is turned off or has died while monitoring, the communication center will pick up on this fact and act accordingly. The system alerts the center when the phone is/shows as either off/out of power (not by user's request) or when the app is non-responsive/inactive, which can automatically be detected by the support center and an automatic or human-generated call/text/alert will be made to the number/program/party indicated by user to notify in case the phone is dead while monitoring, therefore resulting in an inconclusive monitoring. In this case, it could be the user's alternate phone number, email address or the number of another resident of the user's home, user's home phone number, or it could be the number of a neighbor or an apartment manager who will be alerted to go ring the user's bell/knock on the user's door to make sure user is fine and alert user to charge their phone.

The system may further comprise a fall prevention monitoring via education and automatic periodic polling depending on health status. For example, if the reason inputted for malaise is related to the recent ingestion of medication(s) or alcohol, the system will alert/advise the user to sit and not move with rationale for advice. If the system registers a low blood pressure, it will advise the user not to take any blood pressure medication unless it was specifically recommended by their physicians, the same for blood sugar, heart rate and in cases of critical values, the emergency mode would be triggered automatically if user had permitted it. The same way the system alerts users to changes in medical conditions and suggests medical treatment to discuss with a doctor, it will, for example, read user's heart rate and tell the user how his/her pacemaker or artificial heart is doing. Likewise, if a user's oxygen level drops or blood pressure changes dangerously and the user is still alert, the system can recommend steps to take to mediate the problem while waiting for paramedics to arrive. If the patient is incapacitated, the system will notify 911 and the user's loved ones, if the user had requested it.

The system is also capable of teaching about disease management to help users manage their diseases better. Computer software incorporates a complete drug database/reference guide, a complete database of diseases and disease management and remind users to take their medication with full imagery description (from the system drug database) and dosage prescribed. The computer system can also adapt to the user rhythms over time. To manage prescribed medication, a drug reference will be included in the system and the app will be programmed to automatedly detect and link to the reference for the exact picture of a prescribed drug and for teaching purposes and also to double check whether the dosage is right. A schedule with dosage will be set up once by the user or their doctors or their pharmacists to be reminded when drug is due. The app will place a call/text/buzz/alarm to user at user's preferred scheduled time and app will show a large picture of medication for user with vision issues to be able to identify the medication clearly along with the dose prescribed that they have to take, with written or spoken explanation about the drug and on how to take it. There will be linked sections for user to report problems encountered with a particular medication within that medication file. All problems reported by all patients around the world will sync and compute into one public database that will be managed by the system's own Research Center which will also manage the system's Creative Department and also by the system's own Advanced Communication Center. This database can help drugs companies have a global idea of the effects of their drugs on patients and for patients, scientists, students and health professionals to have access to this information as well.

The system and system's API allows doctors access to patient metrics, trends, key data, get info on diseases, on progress, no progress or worsening of conditions, and medications to prescribe. Computer software allows doctors to be able to monitor these metrics in order to titrate or change medications accordingly right from the disease and treatment hub which in turn allows the selection and confirmation of correct dosages directly from the drug database/reference linked to the hub, as well as double verification and reconciliation with other medications as required and then to route it to the user's instantly and send themselves a copy of the prescription to be saved in the patient's virtual folder within the app so that everything that a doctor has ever done for a patient is recorded there along with the patient medical records.

In another embodiment, the computer system is entirely autopilot-able where users need not setup call backs to initiate monitoring but that monitoring happens automatically as the system is able to assess absence of breathing or a pulse, or seizures and others and/or wirelessly and/or remotely monitor vital signs, labs and EKGs values in real-time for signs of distress or absence of life, absence of breathing or heart rate, abnormal breathing & heart rate, seizures using the device's sensors and the human body sensors or any other means appropriate to wirelessly determine and interpret these values accordingly.

Figure 54:
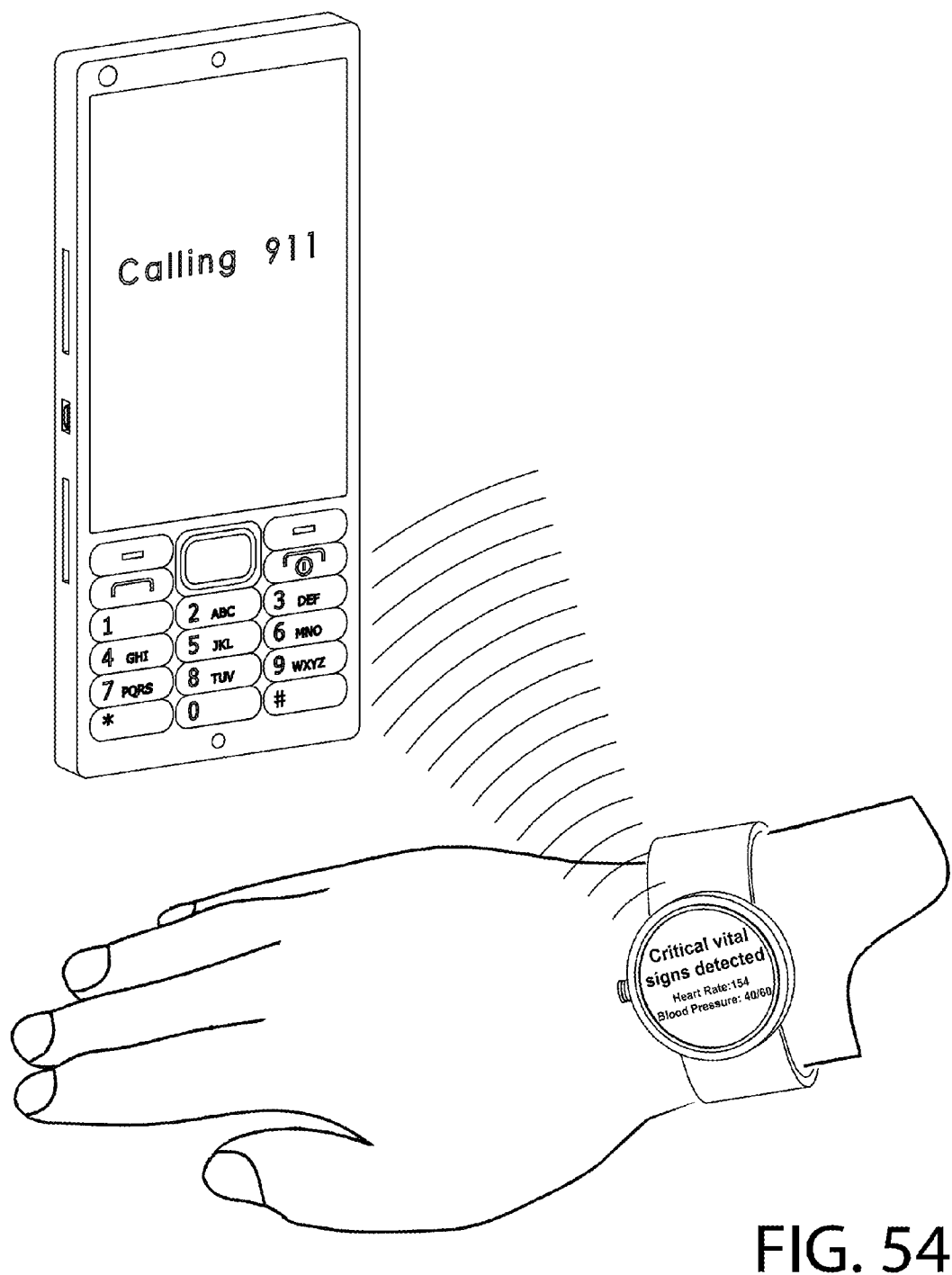

Another embodiment comprises using internal device(s) (such as a pacemaker for example) or external device(s) (such as the system's smartwatch, see FIG. 54; the system's smartwatch sending critical vital signs information to the user's smartphone for ongoing vital signs monitoring) to automatically detect and monitor a user's vital signs for life-threatening critical values. In this embodiment, user's life signs are continually assessed via the system's pacemaker or smartwatch to wirelessly and continuously communicate/transfer/transmit vital signs information to the user's smartphone's system for processing. For example, the smartwatch system monitors the user's vital signs and detects a critical heart rate which represents a threat to the user's life. The smartwatch's system sensors send this information to the user's smartphone on which the present computer system is installed. The smartphone's system upon receiving this information analyzes the data received and determines what steps to take and initiates pre-emergency, monitoring and emergency as applicable. This process works in a similar fashion as when the smartphone's computer system self-initiates emergency monitoring upon receiving critical vital signs information from a third party or proprietary life-signs monitoring device, except that in this embodiment, the vital signs data comes from a pacemaker or a smartwatch. In this case, to make sure that the value is not due to a device malfunction, when an abnormal or critical value is detected, the user can be made aware of it (via alerts or an automatic poll or a phone call from the support center or by any other means appropriate) so that user can take appropriate actions such as double-verify the accuracy of the findings or manually put the system on monitoring mode. If the finding is severe and user is non-responsive to alerts or calls, emergency mode will be automatically and automatedly activated immediately. Another embodiment includes having the system issue prescription on its own without the need for a doctor to manually write this information. The system may further comprise a fall prevention monitoring via education and automatic periodic polling depending on health status. See FIG. 14 for an example of a fall detector device.

CONCLUSION

The aforementioned flowcharts and figure illustrate the architecture, functionality, and operation of possible implementations of systems, methods, and apparatuses comprising computer program products (aka computer code) and/or computer-usable medium having computer-readable program code stored thereon according to various embodiments of the present invention. In this regard, a step(s) in the UML diagrams may represent a module, segment, or portion of code, which comprises one or more executable instructions for implementing the specified logical function(s). It should also be noted that, in some alternative implementations, the functions noted in the diagrams may occur out of the order noted in the Figures. For example, steps shown in succession may, in fact, be executed substantially concurrently, or the steps may sometimes be executed in the reverse order, depending upon the functionality involved. It will also be noted that each step of the UML diagrams, and combinations of steps, can be implemented by special purpose hardware-based systems that perform the specified functions or acts, or combinations of special purpose hardware and computer instructions.

In the above descriptions, an embodiment is an example or implementation of the inventions. The various appearances of "one embodiment," "an embodiment" or "some embodiments" do not necessarily all refer to the same embodiments.

What is claimed is:

1. A computerized method for a user to trigger assistance from a remote computer system in the event of experiencing a potential or on-coming medical emergency, and to automatedly update the user on their current medical condition, comprising the steps of:
   a) activating a monitoring mode by the user on the user's electronic computing device when the user is not feeling well or is concerned about their safety, said device comprising satellite or Internet-based telephone services;
   b) detecting by a remote system processor the user input of settings comprising a time sequence of calls to be made to the user's electronic computing device, wherein the sequence includes frequency of calls to the user's device, and a total time duration for monitoring and before calling the user's emergency contacts and/or an emergency responder service, wherein the user may re-activate the monitoring mode after passage of the total time duration;
   c) calling by the system the user's electronic computing device a first time frequency, and when the user does not respond, then calling a second time frequency, wherein the second time frequency is less than the first time frequency;
   d) activating a pre-emergency mode when the system detects that the user is not responding to a system call within the total time duration for monitoring, and the system calls at least one of the user's emergency contacts;

e) activating an emergency mode when a user's emergency contacts cannot be reached within the total time duration for the pre-emergency mode or when the user needs immediate emergency care, and requesting dispatch of emergency responders to the user's location, and disclosing the following to the emergency responders: a user's medical condition, a user's need for pet, disabled, elderly adult, and/or minor children care, medical insurance, family to contact, and doctor to be notified;

f) providing an authorization code when required, to the emergency responder service, a medical provider or a hospital to access the user's medical records and health data stored on the medical provider's database and on the user's record stored on system database: and g) disclosing the user's legal document stored on the system database when the user or a representative of the user allows it, or an entity provides the system processor with a court order, the legal document including at least two of: a last will and testament, living will, financial accounts information, and life insurance.

2. The computerized method of claim 1, wherein the emergency responder service is contacted in lieu of, or in addition to, the user's emergency contacts if the system processor determines that the user's medical condition requires immediate emergency assistance or the user has allowed or requested it.

3. The computerized method of claim 1, wherein the emergency responder service is contacted if the computer system detects that the user elected not to have the user's emergency contacts contacted, and if the user does not respond to the computer system calls.

4. The computerized method of claim 2, wherein the system processor determines if the user's medical condition requires immediate emergency assistance from data including, one or more current health conditions self-reported, automatedly detected and/or stored in the user's medical records in the system database, one or more medical diagnostic devices in communication with the system, a health history and a sickness patterns.

5. The computerized method of claim 4, further comprising the steps of uploading the data in real-time from one or more of: a medical diagnostic device contact-less or hooked up to the user's electronic computing device; or the medical care provider's records: the data from health monitoring software installed on the user's electronic computing device; the user's implanted medical device and a wearable device that is able to record and monitor a user's vital signs.

6. The computerized method of claim 5, further comprising the steps of monitoring the uploaded data in realtime and, when a critical value is detected, transmitting a message informing the user of the issue and on what to do to resolve the issue, and initiating an automatic call for the emergency responder service.

7. The computerized method of claim 4, further comprising the steps of analyzing data obtained and data on file comprising: medical records, vital signs trends and other data on file and data obtained from a survey so as to alert users to one or more of changes in medical conditions, make a diagnosis or warn the user if there is a risk for diseases and suggest preventive measures to take, and suggest medical treatment to be discussed with a doctor in order for the user to get timely medical treatment.

8. The computerized method of claim 1, further comprising the step of providing to the user a means for recordkeeping, live consultation and treatment suggestion or advice from medical professionals via text, audio and/or video conferencing or via a message to their medical hub, wherein the user can record how they are doing on a daily basis, and how their treatment is progressing.

9. An apparatus including a non-transitory computer readable medium having instructions installed thereon, that when executed by a processing unit, cause the processing unit to provide instructional information to an end user of a software application, by performing the steps of:

a) activating a monitoring mode on the user's electronic computing device when the user is not feeling well or is concerned about their safety, wherein said device comprises satellite or Internet-based telephone services;

b) detecting by a remote system processor the user input of settings comprising a time sequence of system calls made to the user's electronic computing device, wherein the time sequence includes a frequency of calls to user's device, and a total time duration of the calls before activating a pre-emergency mode;

c) calling by the system the user's electronic computing device a first time frequency and a first total time duration, wherein if the user does not respond, then calling a second time frequency and a second total time duration, wherein the first time frequency is longer than the second time frequency;

d) activating the pre-emergency mode when the remote system processor detects that the user is not responding to the system calls within the total time duration of calls, calling at least one of the user's emergency contacts and an emergency responder service;

e) activating an emergency mode when the emergency responder service is contacted, requesting a dispatch of emergency responders to the user's location, and disclosing at least two of the following: the user's medical condition, a current circumstances, a need for pet, minor children, elderly, and disabled adults care, a medical insurance, a family to contact, and a doctor(s) to be notified;

f) when required or allowed by the user, providing an authorization code to the emergency responder service or a hospital to access the user's medical records and health data stored on a medical provider's database and on the user record stored on the system database; and g) disclosing the user's legal document stored on a remote system database when the user or user's representative allows it, or an entity provides the system processor with a court order, the legal document including at least two of: a last will and testament, living will, financial accounts information, and life insurance.

10. The apparatus of claim 9, wherein if the user's medical condition requires immediate emergency assistance, then the system automatically calls the emergency responder server in lieu of the user's emergency contacts.

11. The apparatus of claim 10, further comprising the steps of detecting that the user elects not to have the user's emergency contacts called, and the system calling the emergency responder service if the user does not respond to the computer system calls.

12. The apparatus of claim 10, further comprising the step of the system determining if the user's medical condition requires immediate emergency assistance by evaluating current health conditions that are self-reported or detected via one or more of medical diagnostic devices in communication with the system, a health history and a sickness patterns.

13. The apparatus of claim 12, further comprising the steps of analyzing the data obtained and when a critical value is detected, transmitting a message informing the user on what to do to resolve the issue, and initiating an automatic call for emergency responder service if required.

14. The apparatus of claim 9, further comprising the steps of providing to the user a mechanism for a record-keeping of instructions, plans and ideas required to bring unfinished projects to terms during and after the user's demise, wherein the instructions are stored on a system's project management database, and the mechanism is comparable to the user continuing to work on their projects the same way s/he would if s/he were alive.

15. The apparatus of claim 9, further comprising the steps of providing to the user a mechanism for updating an assigned agent of the progress of unfinished projects within the system's project management database.

16. A network-based computing system for a user to trigger assistance in the event of experiencing a potential or on-coming medical emergency, and to update the user on their current medical condition, the system comprising:
 a. a computer including a processor and a memory device operably connected to one another, and a plurality of computer-executable instructions stored on said memory device such that when the computer-executable instructions are executed by said processor, the instructions cause the processor to perform the steps of:
  i) detecting the user input of settings including time sequence of calls to be made to the user's electronic computing device, wherein the sequence of calls includes a frequency of calls made to the user's device, and total time duration of the calls made to the user's device before calling the user's emergency contacts and/or an emergency responder service;
  ii) when the system detects that the user is not responding to the system call within a pre-specified duration of time, calling at least one of the user's emergency contacts and the emergency responder service when this step is selected; and,
  iii) when the emergency responder service is called, requesting a dispatch of emergency responders to the user's location, and disclosing the user's medical condition, current circumstances, special considerations, need for pet and minor children care, medical insurance, family to contact, and doctor to be notified;
  iv) wherein when required, the processor functions to provide an authorization code to the emergency responder service, a medical provider or a hospital to access the user's updated medical records and health data stored on a medical provider's database and on the user record stored on the system database, wherein the user's record stored on the system comprises the user's most up-to-date medical record and health data uploaded in real-time from the user's latest medical provider visit or hospitalization and thus serving as the user's single consolidated medical record and health data which the medical provider can access regardless of their geographical location; and,
  v) wherein the processor releases the user's legal document stored on the database when the user or their representative has initiated that request to allow it, or an entity provides the system processor with a court order specifying which document to release, the legal document including at least two of: a last will and testament, financial account information, life insurance, and living will;
 b. a database of users' records including for each user, one or more of: medical history, a sensitive medical records requiring authorization code, legal documents, financial account information, and, list of emergency contacts, the database accessible by the system computer;
 c. one or more of user's electronic computing devices, wherein said device comprises satellite or Internet-based telephone services; and,
 d. the network providing communication between the user's electronic computing devices, emergency responders, hospitals, and the system processor.

17. The system of claim 16, wherein the processor functions to determine if the user's medical condition requires immediate emergency assistance from one or more of: the user's current health conditions self-reported and/or detected via medical diagnostic devices in communication with the system, health history and a sickness patterns.

18. The system of claim 17, wherein the processor functions to analyze the data obtained and, when a critical value is detected, the processor further functions to transmit a message informing the user on what to do to resolve the issue, and/or if required, the processor initiates an automatic call for emergency responder service.

* * * * *